US012644109B2

(12) United States Patent
Meng et al.

(10) Patent No.: US 12,644,109 B2
(45) Date of Patent: Jun. 2, 2026

(54) ASPARTIC PROTEASE FOR TREATMENT OF GLUTEN INTOLERANCE, NUCLEIC ACID MOLECULES ENCODING THE ASPARTIC PROTEASE, METHOD OF PRODUCING THE ASPARTIC PROTEASE, AND APPLICATION THEREOF

(71) Applicant: NATIONAL CHUNG HSING UNIVERSITY, Taichung City (TW)

(72) Inventors: Meng Hsiao Meng, Taichung City (TW); Wei Ming Leu, Taichung City (TW); Yu Han Zhang, Taichung City (TW)

(73) Assignee: NATIONAL CHUNG HSING UNIVERSITY, Taichung City (TW)

( * ) Notice: Subject to any disclaimer, the term of this patent is extended or adjusted under 35 U.S.C. 154(b) by 378 days.

(21) Appl. No.: 18/446,301

(22) Filed: Aug. 8, 2023

(65) Prior Publication Data

US 2024/0167012 A1     May 23, 2024

(30) Foreign Application Priority Data

Nov. 17, 2022    (TW) .................................. 111143854

(51) Int. Cl.
| | |
|---|---|
| *C12N 9/60* | (2006.01) |
| *A61K 38/00* | (2006.01) |
| *A61K 38/48* | (2006.01) |

(52) U.S. Cl.
CPC .............. *C12N 9/60* (2013.01); *A61K 38/482* (2013.01); *C12Y 304/23026* (2013.01); *A61K 38/00* (2013.01)

(58) Field of Classification Search
CPC . A61P 1/00; C12Y 304/23; C12Y 304/23026; A68K 38/482; C12N 9/60
See application file for complete search history.

(56) References Cited

FOREIGN PATENT DOCUMENTS

| | | | |
|---|---|---|---|
| WO | WO-2013/083338 A1 | 6/2013 |
| WO | WO-2014/011662 A2 | 1/2014 |
| WO | WO-2017/139659 A1 | 8/2017 |
| WO | WO-2021/013553 A1 | 1/2021 |
| WO | WO-2021/129998 A1 | 7/2021 |

OTHER PUBLICATIONS

Mamo, Jermen, Assefa, Fassil, The Role of Microbial Aspartic Protease Enzyme in Food and Beverage Industries, Journal of Food Quality, 2018, U.S. Pat. No. 7,957,269, 15 pages, 2018. https://doi.org/10.1155/2018/7957269 (Year: 2018).*

* cited by examiner

*Primary Examiner* — Ruth A Davis
(74) *Attorney, Agent, or Firm* — MUNCY, GEISSLER, OLDS & LOWE, P.C.

(57) ABSTRACT

An aspartic protease and the use of the aspartic protease in the hydrolysis of gluten. This protease can hydrolyze gluten and the gluten-derived immunogenic peptides at pH 2.0~4.0. Also provided are methods for the production of the aspartic protease, including recombinant plasmids, transformants, and a purification method thereof; methods of using the aspartic protease to prepare drugs and oral enzyme supplements for treatment of diseases or discomforts related to gluten ingestion, such as celiac disease; and a method of using the asparic protease in food-processing process to remove or reduce gluten in foods or beverages.

6 Claims, 23 Drawing Sheets
Specification includes a Sequence Listing.

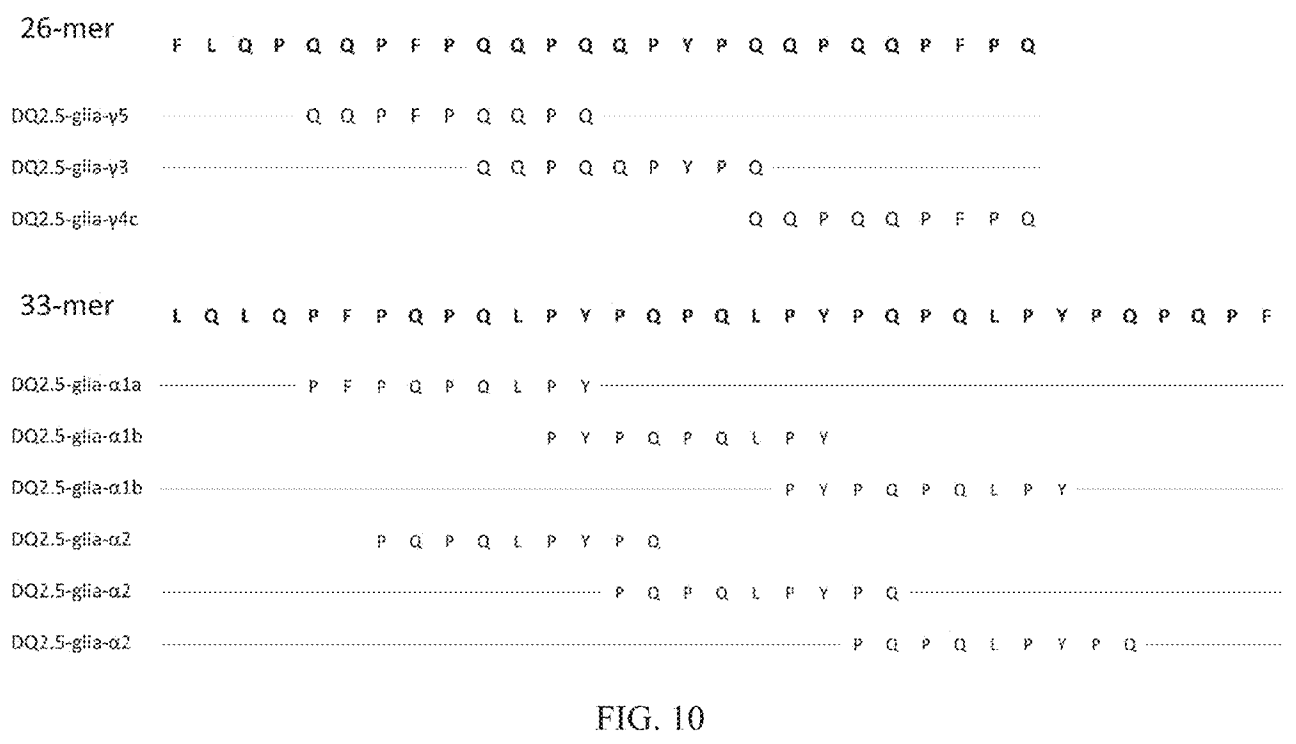

26-mer

DQ2.5-glia-γ5
DQ2.5-glia-γ3
DQ2.5-glia-γ4c 33-mer

DQ2.5-glia-α1a
DQ2.5-glia-α1b
DQ2.5-glia-α1b
DQ2.5-glia-α2
DQ2.5-glia-α2
DQ2.5-glia-α2

FIG. 10

(B) 33-mer

SEQUENCE LISTING

Sequence total quantity: 6
SEQ ID NO: 1               moltype = AA   length = 325
FEATURE                    Location/Qualifiers
source                     1..325
                           mol_type = protein
                           note = "catalytic_domain"
                           organism = Rhodotorula mucilaginosa
SEQUENCE: 1
SLTSYQNDNL WAGKITIGSP AQSFIMDFDT GSSDLWVPSS ACSGSGCGTH ARYTATSSST   60
SKAVTGKTLN VQYGDGSTAS GPVYSDSVTV GGLTATGQTF GTATTLTGNF GSSPSDGLVG   120
MAYPALSQLG VPPFFNTLWS EGRVAANSFS FRLATQNSAA SELYLGGLNS AKYVAGTTGY   180
TPVISQTYWA INTNVAVNGQ AVSGLGTLAA IADTGTTLIV VPTADAQTFW ASVPGAAPYS   240
GGGGYYTFPC NQAPKVTFQF PGSLTKWATP YLNLGTVSYG SNQCVGAIVG QDAGLNAWIL   300
GDSFLKGVYT TFDFANNRVG FSKLA                                        325

SEQ ID NO: 2               moltype = AA   length = 425
FEATURE                    Location/Qualifiers
source                     1..425
                           mol_type = protein
                           organism = Rhodotorula mucilaginosa
REGION                     111..424
                           note = "pepsin_retropepsin_like"
SEQUENCE: 2
MPSFAASAAL ALAVLATANA APVETPSTLA IPLFKRALPK ESRLVDANGV VNFAVLNQTL   60
AGLKGKYHVT QSAAQAHTGR RPFSDGDSQR LARRASTGSD SLTSYQNDNL WAGKITIGSP   120
AQSFIMDFDT GSSDLWVPSS ACSGSGCGTH ARYTATSSST SKAVTGKTLN VQYGDGSTAS   180
GPVYSDSVTV GGLTATGQTF GTATTLTGNF GSSPSDGLVG MAYPALSQLG VPPFFNTLWS   240
EGRVAANSFS FRLATQNSAA SELYLGGLNS AKYVAGTTGY TPVISQTYWA INTNVAVNGQ   300
AVSGLGTLAA IADTGTTLIV VPTADAQTFW ASVPGAAPYS GGGGYYTFPC NQAPKVTFQF   360
PGSLTKWATP YLNLGTVSYG SNQCVGAIVG QDAGLNAWIL GDSFLKGVYT TFDFANNRVG   420
FSKLA                                                              425

SEQ ID NO: 3               moltype = AA   length = 431
FEATURE                    Location/Qualifiers
source                     1..431
                           mol_type = protein
                           organism = Rhodotorula mucilaginosa
SEQUENCE: 3
MPSFAASAAL ALAVLATANA APVETPSTLA IPLFKRALPK ESRLVDANGV VNFAVLNQTL   60
AGLKGKYHVT QSAAQAHTGR RPFSDGDSQR LARRASTGSD SLTSYQNDNL WAGKITIGSP   120
AQSFIMDFDT GSSDLWVPSS ACSGSGCGTH ARYTATSSST SKAVTGKTLN VQYGDGSTAS   180
GPVYSDSVTV GGLTATGQTF GTATTLTGNF GSSPSDGLVG MAYPALSQLG VPPFFNTLWS   240
EGRVAANSFS FRLATQNSAA SELYLGGLNS AKYVAGTTGY TPVISQTYWA INTNVAVNGQ   300
AVSGLGTLAA IADTGTTLIV VPTADAQTFW ASVPGAAPYS GGGGYYTFPC NQAPKVTFQF   360
PGSLTKWATP YLNLGTVSYG SNQCVGAIVG QDAGLNAWIL GDSFLKGVYT TFDFANNRVG   420
FSKLAHHHHH H                                                       431

SEQ ID NO: 4               moltype = DNA   length = 1275
FEATURE                    Location/Qualifiers
source                     1..1275
                           mol_type = genomic DNA
                           organism = Rhodotorula mucilaginosa
SEQUENCE: 4
atgccttcat tcgccgcctc tgccgctctg gcactcgcgg tcctcgctac cgcgaacgcg   60
gctccggtcg agacccettc gactctggcc atcccgttgt ttaagcgggc acttccgaag   120
gaatcgcgcc tcgtcgacgc gaacggcgtc gtcaactttg ccgtcctgaa ccagaccctt   180
gccggcctca agggaaagta ccatgtcacg cagtcggccg ctcaggctca caccgggcgt   240
cgaccgttct ccgacggcga cagccagcga cttgctcgtc gagcctcgac cggttccgac   300
agtctcacgt cttaccagaa tgacaacttg tgggcgggca agatcaccat cggcagcccg   360
gcacagtcct tcatcatgga ctttgacacc ggcagcagtg atctttgggt cccttcgagc   420
gcgtgctccg gctctggctg cggcacgcac gccaggtaca gcctctacgg cctcattgtt   480
tccaaggccg tcactggcaa gaccctcaac gtccagtacg gcgacggttc gaccgcttcc   540
ggaccggtct actccgactc ggtcaccgtc ggcggtttga ccgcgaccgg tcagaccttc   600
ggaacggcga cgaccctcac cggaaacttt ggttcgtcgc ctagcgacgg cctggtcggc   660
atggctacc cggcgctctc gcagctgggc gtcccgacct tcttcaacac gctctggtcc   720
gagggccgcg tcgccgccaa cagcttctcg ttccgcctcg cgacccagaa ctcggccgct   780
tcggagctct acctcggcgg tctcaactcg gccaagtatg tcgccggcac gaccggctac   840
acgcccgtca tctcccagac ttactgggcg atcaacacca acgttgccgt caacggccag   900
gccgttagcg gcctcggcac cctcgcccgc atcgctgaca ctggcacgac cctcattgtt   960
gtcccgactg cggacgctca gaccttctgg gcgagcgttc cgggcgccgc accctactcc   1020
ggcggcggcg gctactacac cttcccgtgc aaccaggccc cgaaggtgac cttccagttc   1080
ccgggctcgt tgaccaagtg ggcgactccg tacctcaacc tcggcacggt ctcgtacggc   1140
agcaaccagt gcgtcggcgc cattgtcggt caggacgctg gtctcaacgc gtggatcctc   1200
ggagacgct ccctcaaggg cgtctacacc actttcgact ttgccaacaa ccgcgtcggc   1260
ttctcgaagc tcgct                                                   1275

SEQ ID NO: 5               moltype = DNA   length = 1293
FEATURE                    Location/Qualifiers -continued

```
source                  1..1293
                        mol_type = other DNA
                        organism = Rhodotorula mucilaginosa
SEQUENCE: 5
atgccttcat tcgccgcctc tgccgctctg gcactcgcgg tcctcgctac cgcgaacgcg  60
gctccggtcg agaccccttc gactctggcc atcccgttgt ttaagcgggc acttccgaag  120
gaatcgcgcc tcgtcgacgc gaacggcgtc gtcaactttg ccgtcctgaa ccagaccctt  180
gccggcctca agggaaagta ccatgtcacg cagtcggccg ctcaggctca caccgggcgt  240
cgaccgttct ccgacggcga cagccagcga cttgctcgtc gagcctcgac cggttccgac  300
agtctcacgt cttaccagaa tgacaacttg tgggcgggca agatcaccat cggcagcccg  360
gcacagtcct tcatcatgga ctttgacacc ggcagcagtg atctttgggt cccttcgagc  420
gcgtgctccg gctctggctg cggcacgcac gccaggtaca cggccacgtc gtcctcgacg  480
tccaaggccg tcactggcaa gaccctcaac gtccagtacg gcgacggttc gaccgcttcc  540
ggaccggtct actccgactc ggtcaccgtc ggcggtttga ccgcgaccgg tcagaccttc  600
ggaacggcga cgaccctcac cggaaacttt ggttcgtcgc ctagcgacgg cctggtcggc  660
atggcctacc cggcgctctc gcagctgggc gtcccgccct tcttcaacac gctctggtcc  720
gagggccgcg tcgccgccaa cagcttctcg ttccgcctcg cgacccagaa ctcggccgct  780
tcggagctct acctcggcgg tctcaactcg gccaagtatg tcgccggcac gaccggctac  840
acgcccgtca tctcccagac ttactgggcg atcaacacca acgttgccgt caacggccag  900
gccgttagcg gcctcggcac cctcgccgcg atcgctgaca ctggcacgac cctcattgtt  960
gtcccgactg cggacgctca gaccttctgg gcgagcgttc cgggcgccgc accctactcc  1020
ggcggcggcg gctactacac cttcccgtgc aaccaggccc cgaaggtgac cttccagttc  1080
ccgggctcgt tgaccaagtg ggcgactccg tacctcaacc tcggcacggt ctcgtacggc  1140
agcaaccagt gcgtcggcgc cattgtcggt caggacgctg gtctcaacgc gtggatcctc  1200
ggagacagct tcctcaaggg cgtctacacc actttcgact ttgccaacaa ccgcgtcggc  1260
ttctcgaagc tcgctcatca tcatcaccac cac                               1293

SEQ ID NO: 6               moltype = AA   length = 13
FEATURE                    Location/Qualifiers
source                     1..13
                           mol_type = protein
                           note = "Active site flap [active]"
                           organism = Rhodotorula mucilaginosa
SEQUENCE: 6
NVQYGDGSTA SGP                                                      13
```

ASPARTIC PROTEASE FOR TREATMENT OF GLUTEN INTOLERANCE, NUCLEIC ACID MOLECULES ENCODING THE ASPARTIC PROTEASE, METHOD OF PRODUCING THE ASPARTIC PROTEASE, AND APPLICATION THEREOF

CROSS-REFERENCE TO RELATED APPLICATIONS

This application claims the benefit of priority to Taiwan Patent Application No. 111143854, filed on Nov. 17, 2022. The entire content of the above-identified application is incorporated herein by reference.

REFERENCE TO AN ELECTRONIC SEQUENCE LISTING

The content of the electronic sequence listing (2023-08-08-Seq-Listing.xml; Size: 10,791 bytes; and Date of Creation: Aug. 8, 2023) is herein incorporated by reference in its entirety.

BACKGROUND

Technical Field

The present disclosure relates to a protease with proteolytic activity in an acidic environment, and more particularly, to an aspartic protease being able to hydrolyze gluten and the application thereof.

Description of Related Art

Gluten is a protein that naturally exists in grains such as wheat, barley, and rye, and is commonly found in foods such as bread, biscuits, or cakes. Gluten can give foods elastic and chewy properties, but gluten is highly resistant to the digestive processes in the human stomach. Celiac disease (CD) is an autoimmune disease caused by ingestion of gluten. The main protein in gluten that causes celiac disease is gliadin, which contains proline and glutamine amino acids and is resistant to hydrolysis by proteases. Therefore, the gliadin not completely digested by pepsin is degraded into multiple gluten immunogenic peptides. After being absorbed in the duodenum, the gluten immunogenic peptides are easily bound to T-cells and cause an immune response, leading to malabsorption of intestinal villi. Typical symptoms include diarrhea, bloating, and abdominal cramping.

Oral protease therapy is a potential adjuvant therapy for celiac disease. Oral proteases to assist a gluten-free diet need to be active in the acidic environment of the human stomach (pH 2.0-4.0) and can rapidly cleave gluten immunogenic peptides before the gluten immunogenic peptides enter the duodenum and trigger an immune response. However, many studies have indicated that the many celiac disease protease supplements on the market are ineffective in the cleavage of T-cell epitopes on gluten immunogenic peptides in an acidic environment. Therefore, there is a need for a new protease, which is not only resistant to pepsin, but also can hydrolyze gluten in the gastric acid environment, and can effectively cleave the epitopes of immunogenic peptides.

BRIEF SUMMARY OF THE INVENTION

Therefore, it is an object of the present disclosure to provide a method for treating gluten intolerance by utilizing an aspartic protease including an amino acid sequence having at least 70% identity to the sequence identified as SEQ ID NO: 1, SEQ ID NO: 2, or SEQ ID NO: 3, wherein the aspartic protease has gluten-degrading activity between pH 2.0 and pH 4.0, and the method includes a step of administering the aspartic protease to a patient in need.

According to an embodiment of the present disclosure, wherein the amino acid sequence of the aspartic protease has at least 80% identity to the sequence identified as SEQ ID NO: 1, SEQ ID NO: 2, or SEQ ID NO: 3.

According to an embodiment of the present disclosure, wherein the amino acid sequence of the aspartic protease has at least 90% identity to the sequence identified as SEQ ID NO: 1, SEQ ID NO: 2, or SEQ ID NO: 3.

According to an embodiment of the present disclosure, wherein the optimum pH value of utilizing the aspartic protease on degrading gliadin is pH 2.5.

According to an embodiment of the present disclosure, the method further includes utilizing the aspartic protease to cleave epitopes on gluten immunogenic peptides 26-mer or 33-mer.

According to an embodiment of the present disclosure, wherein the amino acid sequence of the aspartic protease includes at least 90% identity to the sequence identified as SEQ ID NO:6.

According to an embodiment of the present disclosure, wherein the aspartic protease further includes a histidine tag.

Another object of the present disclosure is to provide a nucleic acid molecule for encoding the aspartic acid protease for treating gluten intolerance, wherein the nucleic acid molecule includes a sequence selected from the group consisting of:

(a) a nucleotide sequence with at least 70% identity to the sequence identified as SEQ ID NO: 4; and (b) a nucleotide sequence with at least 70% identity to the sequence identified as SEQ ID NO:5.

Still another object of the present disclosure is to provide a recombinant plasmid, including the aforementioned nucleic acid molecule and a regulatory sequence capable of initiating production of protein encoded by the nucleic acid molecule.

Still yet another object of the present disclosure is to provide a transformant with the aforementioned recombinant plasmid, wherein the transformant includes a yeast cell.

According to an embodiment of the present disclosure, wherein the transformant includes *Yarrowia lipolytica*.

Even still another object of the present disclosure is to provide a method for producing an aspartic protease, including steps of:

constructing a recombinant plasmid containing the aforementioned nucleic acid molecule, wherein the nucleic acid molecule includes a histidine tag;

forming a transformant with the recombinant plasmid;

cultivating the transformant with a liquid culture medium, wherein the transformant produces the aspartic protease in the liquid culture medium; and purifying the liquid culture medium to obtain the aspartic protease.

According to an embodiment of the present disclosure, wherein the liquid culture medium includes peptone, yeast extract, and glycerol.

According to an embodiment of the present disclosure, wherein the step of purifying the liquid culture solution to obtain the aspartic protease includes:

collecting supernatant from the liquid culture medium, and adding a binding buffer at a volume ratio of 1:10 to form a first mixed solution, and equilibrate on ice;

wherein, the binding buffer is composed of sodium phosphate, sodium chloride, and imidazole, of pH 6.0;

percolating the first mixed solution with an immobilized metal ion affinity chromatography column containing divalent cations;

washing proteins that are not bound to the immobilized metal ion affinity chromatography column containing divalent cations by using the binding buffer; and eluting the aspartic protease from the immobilized metal ion affinity chromatography column by using a second mixed solution formed by 60% binding buffer and 40% 0.1M glycine-hydrochloric acid and having a pH value of 2.5.

According to an embodiment of the present disclosure, wherein the immobilized metal ion affinity chromatography column includes nickel columns.

According to an embodiment of the present disclosure, further includes a step of forming an enzyme supplement by utilizing the aspartic protease and providing the enzyme supplement to the patient in need.

Further another object of the present disclosure is to provide an enzyme supplement for metabolizing gluten-containing foods, including an aspartic protease having an amino acid sequence having at least 70% identity to the sequence identified as SEQ ID NO: 1, SEQ ID NO: 2, or SEQ ID NO: 3; wherein, the aspartic protease has gluten-degrading activity between pH 2.0 and pH 4.0.

According to an embodiment of the present disclosure, wherein the amino acid sequence of the aspartic protease includes at least 90% identity to the sequence identified as SEQ ID NO:6.

According to an embodiment of the present disclosure, wherein the maximum activity of the aspartic protease on gliadin is at pH 2.5.

According to an embodiment of the present disclosure, wherein the aspartic protease is produced by a transformant including *Yarrowia lipolytica*.

In summary, the aspartic protease of the present disclosure has the following advantages: (1) the aspartic protease has proteolytic activity in the acidic environment of the human stomach; (2) the aspartic protease can assist the hydrolysis of pepsin; (3) the aspartic protease can hydrolyze gluten immunogenic peptides. The aspartic protease of the present disclosure can be used to prepare medicines or protease (enzyme) supplements for treating diseases such as celiac disease, gluten allergy, or gluten intolerance.

BRIEF DESCRIPTION OF THE DRAWINGS

FIG. 10 is a schematic diagram of the T-cell epitopes on the gluten immunogenic peptide sequences;

DETAILED DESCRIPTION OF THE INVENTION

Figure 1:
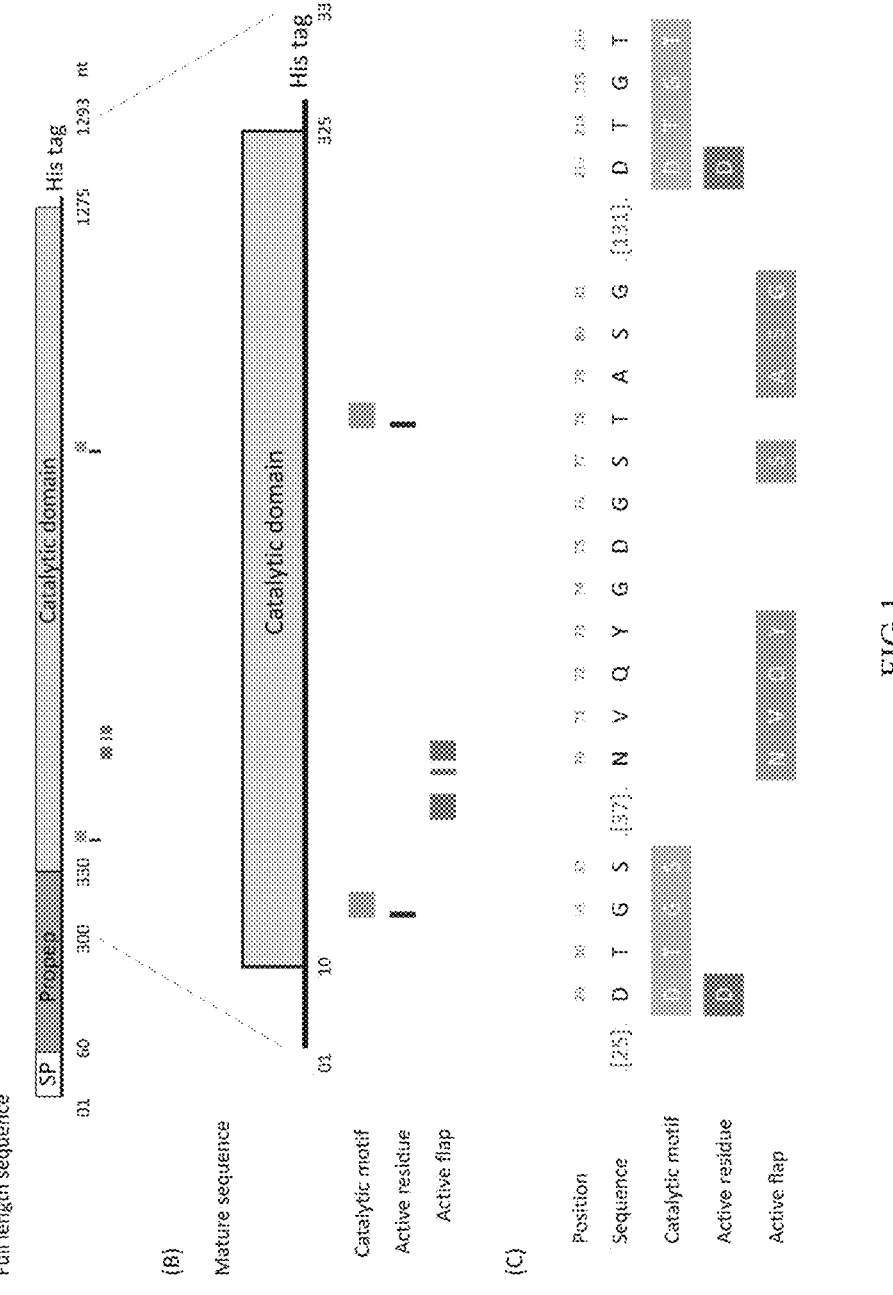
FIG. 1 is a schematic diagram of the gene composition of the aspartic protease Rhodotorulapepsin according to the present disclosure.

As mentioned above, although several types of proteases capable of hydrolyzing gluten have been disclosed, most of the proteases disclosed in the prior art cannot have good activity in the acidic environment of the human stomach (pH2.0-4.0); or the proteases cannot effectively cleave the T-cell epitopes of the gluten immunogenic peptides. Therefore, the application of the proteases disclosed by the prior art is limited and cannot be used as an effective protease supplement for gluten autoimmune patients.

Strain Screening

The inventors cultivated various kinds of strains capable of secreting proteases and then screened out the strains which can secrete proteases having activity in an acidic environment. The strains were cultured by using the YPD medium of the formula shown in Table 1 at 28° C., 200 rpm for four days. Then, the supernatant containing proteases was collected from the culture medium. A solid-state activity disc was prepared by suspending gliadin in 50 mM McIl-vaine buffer solution (pH3.0), and then the solid-state activity disc was utilized to screen out the protease with the highest hydrolytic activity on gliadin. The protease with the highest hydrolytic activity from the screening result was identified, and the DNA of the protease was confirmed as being secreted by *Rhodotorula mucilaginosa*. *Rhodotorula mucilaginosa* can be purchased from the market through organizations such as Food Industry Research and Development Institute.

| Content | Weight | Concentration |
| --- | --- | --- |
| Peptone | 20 g | 20 g/L |
| Yeast Extract | 10 g | 10 g/L |
| Dextrose | 20 g | 20 g/L |

Amino Acid Sequence of Aspartic Protease Rhodotorulapepsin

The protease obtained from the above strain-screening experiment was confirmed to be an aspartic protease through data comparison with the database of the National Center for Biotechnology Information (NCBI). Then, the screened protease was named Rhodotorulapepsin (R.AsP) by the inventors. The amino acid sequence of the aspartic protease Rhodotorulapepsin is represented by SEQ ID NO: 2, including 425 amino acids. The amino acid sequence of a mature aspartic protease Rhodotorulapepsin is represented by SEQ ID NO: 1, including 325 amino acids. According to the present disclosure, a recombinant plasmid and a transformant (see detailed description below) were prepared to produce an aspartic protease Rhodotorulapepsin. The produced aspartic protease Rhodotorulapepsin further includes a histidine tag (His-Tag), and the amino acid sequence of the produced aspartic protease Rhodotorulapepsin is represented by SEQ ID NO: 3, including 431 amino acids. According to the present disclosure, the aspartic protease Rhodotorulapepsin for use in the hydrolysis of gluten includes an amino acid sequence selected from the group consisting of an amino acid sequence having at least 70%, preferably at least 75%, more preferably at least 80%, even more preferably at least 85%, even more preferably 90%, even more preferably 95% or even more preferably 100% identity to the sequence identified as SEQ ID NO: 1; an amino acid sequence having at least 70%, preferably at least 75%, more preferably at least 80%, even more preferably at least 85%, even more preferably 90%, even more preferably 95% or even more preferably 100% identity to the sequence identified as SEQ ID NO: 2; and an amino acid sequence having at least 70%, preferably at least 75%, more preferably at least 80%, even more preferably at least 85%, even more preferably 90%, even more preferably 95% or even more preferably 100% identity to the sequence identified as SEQ ID NO: 3.

The present disclosure also provides a nucleic acid molecule for encoding the aspartic protease Rhodotorulapepsin. The nucleic acid molecule includes a sequence selected from the group consisting of a nucleotide sequence having at least 70%, preferably at least 75%, more preferably at least 80%, even more preferably at least 85%, even more preferably at least 95%, or even more preferably 100% identity to the sequence identified as SEQ ID NO: 4; and a nucleotide sequence having at least 70%, preferably at least 75%, more preferably at least 80%, even more preferably at least 85%, even more preferably at least 95%, or even more preferably 100% identity to the sequence identified as SEQ ID NO: 5.

As shown in FIG. 1, (A) is the structure of the nucleic acid molecule for use in encoding the aspartic protease Rhodotorulapepsin, which has a nucleotide sequence represented by SEQ ID NO: 4, includes an N-terminal signal peptide (1-60), a propeptide (61-330) and an aspartic protease catalytic domain (331-1275). The catalytic domain of the aspartic protease shown in the figure represents an active fragment of the aspartic protease Rhodotorulapepsin. The structure of the mature aspartic protease Rhodotorulapepsin does not include the signal peptide and most of the propeptide. As shown in FIG. 1, (B) is the mature aspartic protease Rhodotorulapepsin including the active fragment, and the sequence of the active fragment was analyzed by using the InterPro database. From the analysis result, the structure of the mature aspartic protease Rhodotorulapepsin includes a catalytic motif, an active residue, and a flap region, wherein the amino acid sequences thereof are shown as (C) in FIG. 1. The amino acid sequence of the catalytic motif of the aspartic protease Rhodotorulapepsin includes DTGS (29-32) and DTGT (213-216); the amino acid sequence of the active residue of the aspartic protease Rhodotorulapepsin includes two Asp residues (D29 and D213); the amino acid sequence of the flap region of the aspartic protease Rhodotorulapepsin includes NVQYGDGSTASGP (70-82). The detailed sequence of the flap region is represented by SEQ ID NO:6. The flap region is like a movable cap covering the active residue, which participates in the cleavage reaction of the proteases. The presence of hydrolytic activity is specific to the position of the flap region, while the substrate specificity is related to the amino acid sequence of the flap region.

Recombinant Plasmid

The present disclosure also provides a recombinant plasmid including the nucleic acid molecule for encoding the aspartic protease Rhodotorulapepsin. In the present embodiment, a yeast expression kit, which was purchased from YEASTERN BIOTECH CO., LTD., was used to construct the recombinant plasmid, but the present disclosure is not limited thereto. The method for constructing the recombinant plasmid first included a step of designing a pair of primers (as shown below; the underlined nucleotides are the cleavage sites of the restriction enzymes PmlI and KpnI respectively).

[5'-CACGTGAATGCC TTCATTCGCCGCCTCTGCCGC-3'];
and

[5'-GGAGGTACCTTAAGCGAGCTTCGAGA AGCCG-3']

Figure 2:
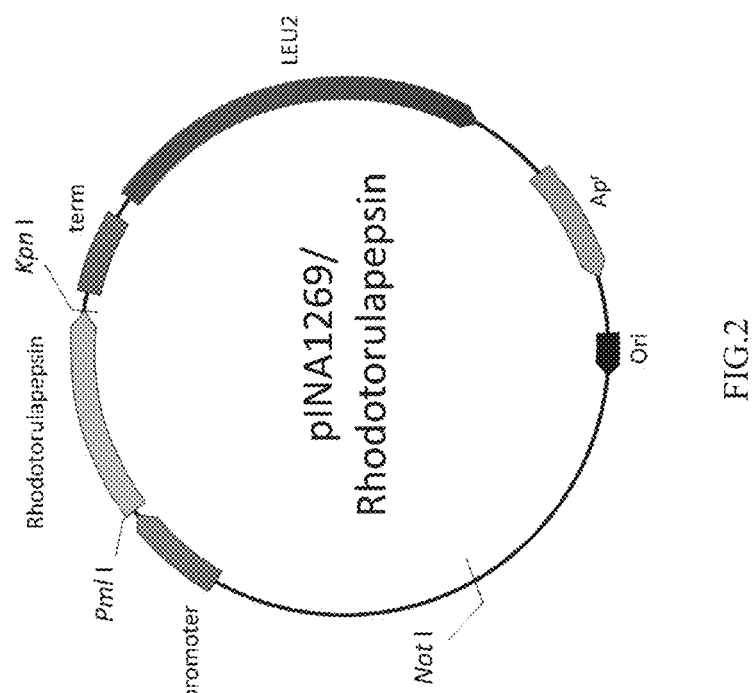
FIG. 2 is a schematic diagram of the recombinant plasmid according to the present disclosure, which includes the nucleotide sequences of the aspartic protease.

Next, the coding sequence of the aspartic protease R.AsP from the cDNA of *Rhodotorula mucilaginosa* was amplified, and then a histidine tag (His-Tag) was added to the DNA 3'-end of the amplified aspartic protease R.AsP sequence by the PCR method. The nucleotide sequence of the aspartic protease R.AsP with His-Tag is represented by SEQ ID NO:5. Then, the amplified sequence of the aspartic protease R.AsP was constructed in an expression vector (7259 bp) to form a recombinant plasmid pINA1269/Rhodotorulapepsin. FIG. 2 is a schematic diagram of the recombinant plasmid according to the present disclosure. The recombinant plasmid pINA1269/Rhodotorulapepsin includes a regulatory sequence and the nucleotide sequence of the aspartic protease R.AsP. The regulatory sequence can promote protein expression of the nucleotide sequence of the aspartic acid R.AsP in specific cells. In the present embodiment, the regulatory sequence includes a promotor (hp4d Promoter), a terminator (XPR2 Terminator), a leucine synthesis gene (LEU2), an ampicillin resistance gene (Apr), and an origin of replication (Ori). The gene of the aspartate protease Rhodotorulapepsin was cloned between PmlI and KpnI.

In the present embodiment, the recombinant plasmid was constructed by using pINA1269 as an example, but the present disclosure is not limited thereto, other options such as a plasmid pETDuet-1 can also be used for constructing a recombinant plasmid.

The Method of Producing the Aspartic Protease R.AsP

Transformants

The present disclosure provides a transformant for producing the aspartic protease Rhodotorulapepsin. In the present embodiment, *Yarrowia lipolytica* (*Y. lipolytica*) was selected as a host cell for the production of recombinant proteins. *Y. lipolytica* is classified as Generally Recognized as Safe (GRAS) by the U.S. Food and Drug Administration (FDA). The protein produced by the GRAS strain can be used as food and can be labeled as having no side effects or without any warning or restrictions on use. In the present embodiment, a yeast expression kit containing *Yarrowia lipolytica* Po1g was utilized, wherein the yeast expression kit was purchased from YEASTERN BIOTECH CO., LTD. *Yarrowia lipolytica* Po1g was used as a host cell for the production of recombinant proteins.

In the present embodiment, *Yarrowia lipolytica* Po1g was utilized as a host cell as an example, but the present disclosure is not limited thereto. For example, when the plasmid is pETDuet-1, other strains such as *E. coli* BL21 (DE3), *E. coli* BL21 star (DE3), *E. coli* BL21 star (DE3) pRARE, *E. coli* Rosetta pRARE (DE3), *E. coli* Rosetta pRARE (DE3) pLysS, *E. coli* NovaBlue (DE3), *E. coli* C41 (DE3) pLysS and *E. coli* C43 (DE3) pLysS can be utilized as host cells; when the plasmid is pINA1269 or pYLSC1, *Yarrowia lipolytica* Po1g can be used as the host cell; when the plasmid is pPICZaA or pPICZaB, *Pichia pastoris* X-33 can be utilized as host cells.

After the recombinant plasmid pINA1269/Rhodotorulapepsin was produced, the circular molecules of the recombinant plasmid pINA1269/Rhodotorulapepsin was converted into linear molecules by restriction enzymes. The linear molecules were then used as a target gene. The target gene was inserted into the chromosome of *Yarrowia* yeast by homologous recombination to form a transformant. The transformant having the target gene was cultured at 28° C. and 200 rpm by using the YPG medium shown in Table 2.

TABLE 2

| Content | Quantity | Concentration |
| --- | --- | --- |
| Peptone | 20 g | 20 g/L |
| Yeast Extract | 10 g | 10 g/L |
| Glycerol | 20 ml | 2% |

Expression of Aspartic Protease Rhodotorulapepsin in the Transformant

Figure 3:
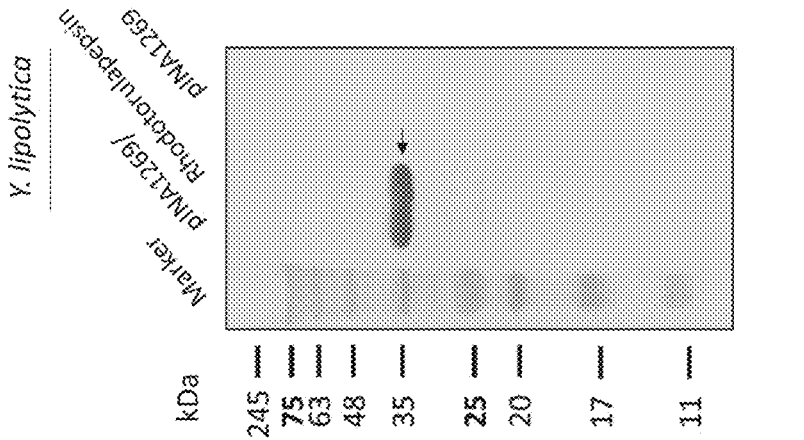
FIG. 3 is the Western blot analysis result of the aspartic protease Rhodotorulapepsin according to the present disclosure.

By culturing the transformant having the target gene, the mature aspartic protease Rhodotorulapepsin produced by the transformant would be naturally accumulated in the liquid culture medium of the transformant. Referring to FIG. 3, showing the Western blot analysis result of the aspartic protease Rhodotorulapepsin, the size of active aspartic protease Rhodotorulapepsin is about 33 kDa, wherein a rabbit anti-6×His antibody was used as a primary antibody and a goat anti-rabbit antibody-AP was used as a secondary antibody.

The transformant was cultivated in the liquid culture medium for four days and then centrifuged to remove the cell pellets. The supernatant obtained from the liquid culture medium was used for subsequent purification steps.

The Purification Method of the Aspartic Protease Rhodotorulapepsin

Immobilized metal ion affinity chromatography (IMAC) column containing divalent cations can be utilized to purify the histidine-tagged aspartic protease Rhodotorulapepsin. In the present embodiment, a nickel column for immobilized metal affinity chromatography (IMAC) was utilized to purify the obtained supernatant. The method includes the following steps. First, a binding buffer (pH 6.0) as shown in Table 3, which was composed of 20 mM sodium phosphate, 0.5 mM sodium chloride, and 40 mM imidazole, was added to the supernatant containing the aspartic protease Rhodotorulapepsin in a volume ratio of 10:1 to form a first mixed solution. The first mixed solution was equilibrated on ice for 30 minutes. Next, the first mixed solution was added to bind with the Ni-NTA (a nickel-based nitrilotriacetic acid) resin inside of the nickel column for 1 hour. Then, unbound proteins were washed out from the Ni-NTA resin using the binding buffer in a volume ratio of 1:1. Thereafter, the aspartic protease Rhodotorulapepsin was eluted from the column by using a second mixed solution formed of 60% binding buffer solution and 40% 0.1M glycine-HCl (pH 2.5). The obtained aspartic protease Rhodotorulapepsin can be concentrated with a 10 kDa filter membrane and then dialyzed with 50 mM McIlvaine buffer solution (pH 5.0) for preservation.

| Composition | Concentration |
| --- | --- |
| Sodium Phosphate | 20 mM |
| Sodium Chloride | 0.5M |
| Imidazole | 40 mM |

Figure 4A:
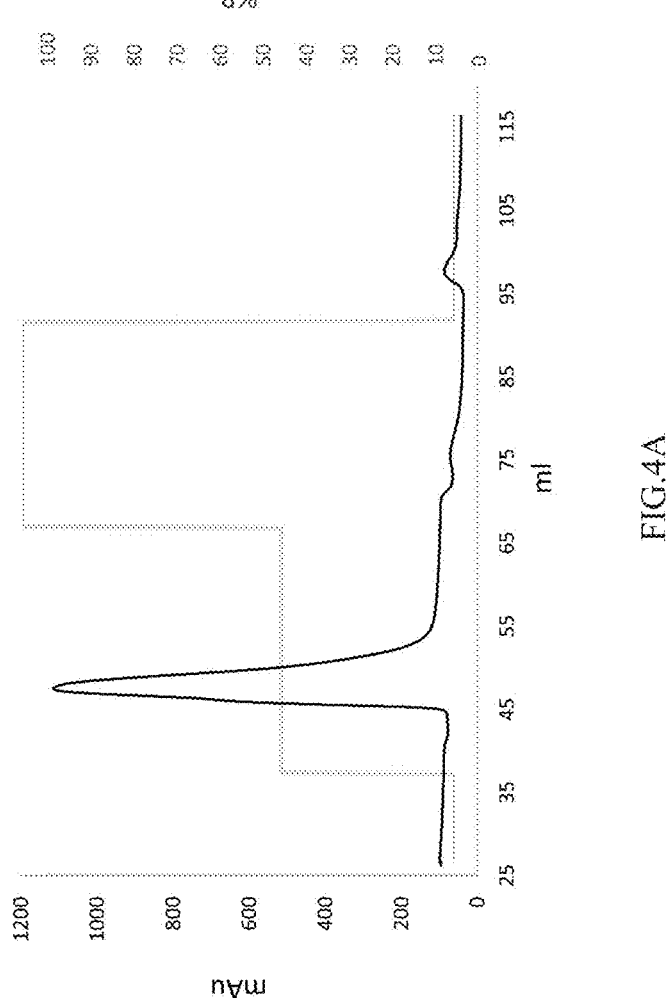
FIG. 4A is the chromatogram of the aspartic protease Rhodotorulapepsin purified by IMAC.
Figure 4B:
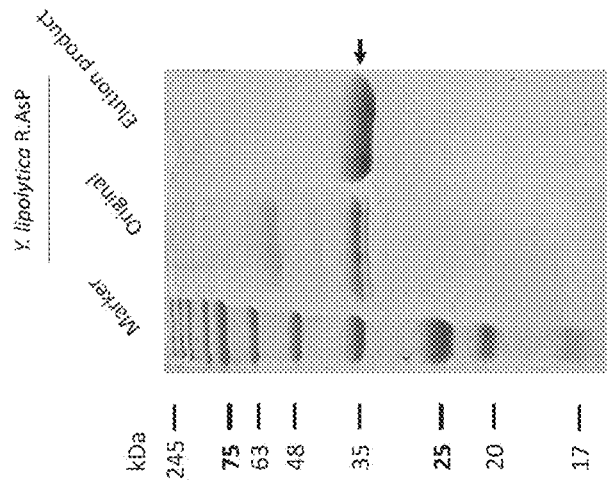
FIG. 4B is the diagram of SDS-PAGE analysis result of the protein solutions before and after purification.

FIG. 4A is the diagram showing a chromatogram of the aspartic protease Rhodotorulapepsin purified by IMAC, wherein the aspartic protease Rhodotorulapepsin is eluted as a peak at 50 ml of the buffer solution. FIG. 4B is the diagram showing the results of SDS-polyacrylamide gel electrophoresis (SDS-PAGE) analysis of the protein solutions before and after purification, wherein Lane 2 represents the total protein (Original) before separation and purification, and Lane 3 represents the eluted (purified) aspartic protease Rhodotorulapepsin (Elution Product); the arrow denotes the mature aspartic protease Rhodotorulapepsin.

Characteristic Analysis of Aspartic Protease Rhodotorulapepsin

In the present embodiment, several experiments were performed to analyze the characteristics of the aspartic protease Rhodotorulapepsin according to the present disclosure. In the experiments, bovine serum albumin (BSA, purchased from Sigma-Aldrich, the U.S.) was used as the protein to be hydrolyzed, and the aspartic protease Rhodotorulapepsin according to the present disclosure was used as the enzyme to hydrolyze the protein. The hydrolysis reactions were performed at different temperatures and pH conditions such that the optimal reaction conditions and stability of the aspartic protease Rhodotorulapepsin were found. In the following experiments, when each of the reactions was completed, the reaction was stopped with 10% (w/v) trichloroacetic acid (TCA). Then, the reaction solutions were centrifugated to remove the precipitate. The absorbance at 280 nm of the reaction solutions was measured by a spectrophotometer to determine the relative activity of the aspartic protease Rhodotorulapepsin and pepsin under different experimental conditions.

(1) the Optimum pH Value Analysis:

Experiment 1: The aspartic protease Rhodotorulapepsin and BSA were mixed in buffer solutions with different pH values of pH 1.0 to pH 8.0 (see Table 4), and reacted at a temperature of 37° ° C. for 1 hour.

TABLE 4

| Experimental Condition | BSA Concen- tration | Rhodotorulapepsin Concentration | pH value | Buffer Solution |
|---|---|---|---|---|
| (1) | 5 mg/ml | 10 µg/ml | 1.0 | 50 mM K/HCl |
| (2) | 5 mg/ml | 10 µg/ml | 1.5 | 50 mM K/HCl |
| (3) | 5 mg/ml | 10 µg/ml | 2.2 | 50 mM K/HCl |
| (4) | 5 mg/ml | 10 µg/ml | 2.2 | 50 mM Glycine-HCl |
| (5) | 5 mg/ml | 10 µg/ml | 2.5 | 50 mM Glycine-HCl |
| (6) | 5 mg/ml | 10 µg/ml | 2.5 | 50 mM McIlvaine |
| (7) | 5 mg/ml | 10 µg/ml | 3.0 | 50 mM Glycine-HCl |
| (8) | 5 mg/ml | 10 µg/ml | 3.0 | 50 mM McIlvaine |
| (9) | 5 mg/ml | 10 µg/ml | 4.0 | 50 mM McIlvaine |
| (10) | 5 mg/ml | 10 µg/ml | 5.0 | 50 mM McIlvaine |
| (11) | 5 mg/ml | 10 µg/ml | 6.0 | 50 mM McIlvaine |

10

TABLE 4-continued

| Experimental Condition | BSA Concen- tration | Rhodotorulapepsin Concentration | pH value | Buffer Solution |
|---|---|---|---|---|
| (12) | 5 mg/ml | 10 µg/ml | 7.0 | 50 mM McIlvaine |
| (13) | 5 mg/ml | 10 µg/ml | 8.0 | 50 mM McIlvaine |

Figure 5A:
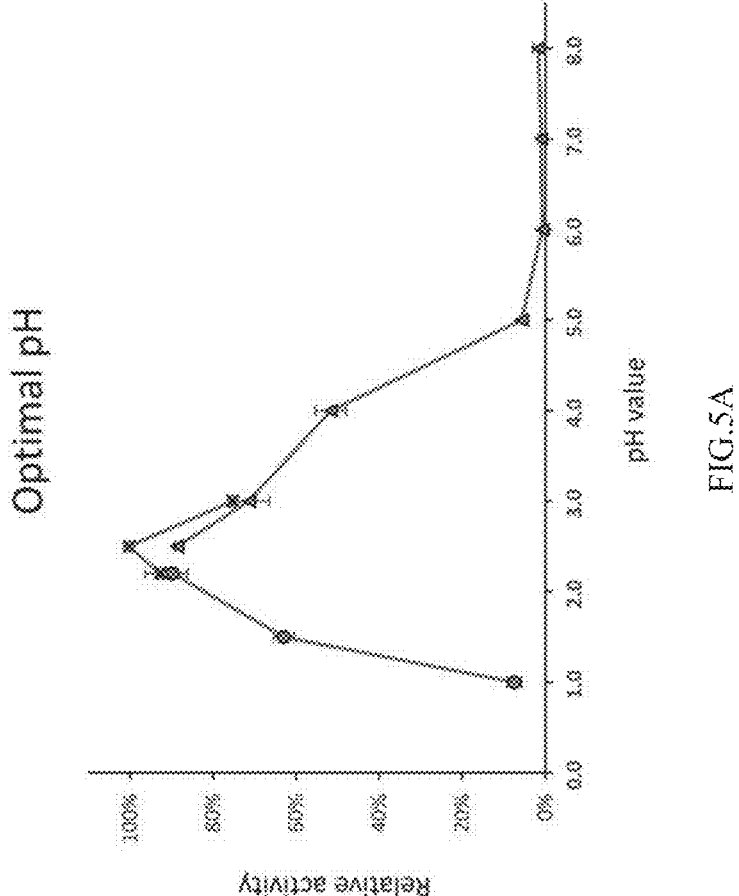
FIG. 5A is an analysis chart showing the relative activity of the aspartic protease Rhodotorulapepsin under different pH conditions according to Experiment 1.

Referring to FIG. 5A, showing a relative activity analysis chart of the aspartic protease Rhodotorulapepsin under different pH conditions. As shown in the chart, the aspartic protease Rhodotorulapepsin has good proteolytic activity at a range of pH 2.0 to pH 4.0; preferably, the maximum proteolytic activity of the aspartic protease Rhodotorulapepsin was found at pH 2.5.

(2) Analysis of pH Stability:

Experiment 2: The aspartic protease Rhodotorulapepsin was mixed in buffer solutions of different pH values including pH 1.0, pH 1.5, pH 2.2, pH 2.5, pH 3.0, pH 4.0, pH 5.0, pH 6.0, pH 7.0 and pH 8.0 (see Table 5) at a temperature of 37° ° C. for 3 hours. Next, the solutions containing the aspartic protease Rhodotorulapepsin were respectively adjusted to pH 2.5 with 50 mM McIlvaine buffer solution (pH 2.5). Then, BSA was added into each of the buffer solutions to react with the aspartic protease Rhodotorulapepsin for 1.5 hours, wherein, the concentration of BSA is 5 mg/ml.

TABLE 5

| Experimental Conditions | Rhodotorulapepsin Concentration | pH value | Temper- ature | Buffer Solution |
|---|---|---|---|---|
| (1) | 10 µg/ml | 1.0 | 37° C. | 50 mM K/HCl |
| (2) | 10 µg/ml | 1.5 | 37° C. | 50 mM K/HCl |
| (3) | 10 µg/ml | 2.2 | 37° C. | 50 mM K/HCl |
| (4) | 10 µg/ml | 2.5 | 37° C. | 50 mM McIlvaine |
| (5) | 10 µg/ml | 3.0 | 37° C. | 50 mM McIlvaine |
| (6) | 10 µg/ml | 4.0 | 37° C. | 50 mM McIlvaine |
| (7) | 10 µg/ml | 5.0 | 37° C. | 50 mM McIlvaine |
| (8) | 10 µg/ml | 6.0 | 37° C. | 50 mM McIlvaine |
| (9) | 10 µg/ml | 7.0 | 37° C. | 50 mM McIlvaine |
| (10) | 10 µg/ml | 8.0 | 37° C. | 50 mM McIlvaine |

Figure 5B:
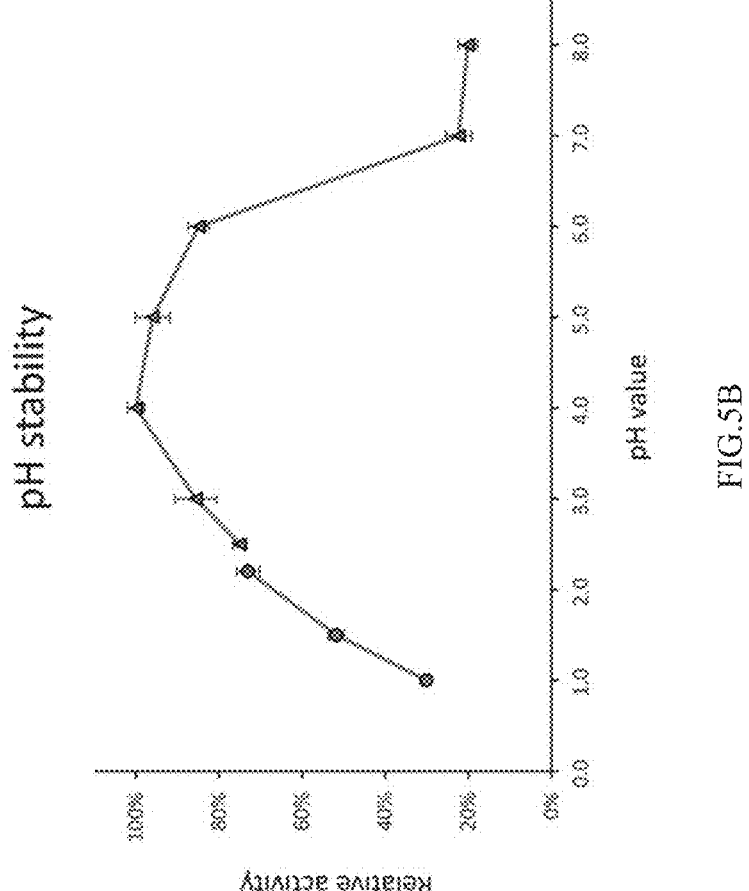
FIG. 5B is an analysis chart showing the stability of the aspartic acid protease Rhodotorulapepsin under different pH conditions according to Experiment 2.

Referring to FIG. 5B, showing a stability analysis chart of the aspartic acid protease Rhodotorulapepsin under different pH conditions. As shown in the chart, the aspartic acid protease Rhodotorulapepsin has a relative stability of 52% to 100% at the acidic pH environment, i.e., pH2.0 to pH4.0, of the human stomach.

(3) Analysis of the Optimum Reaction Temperature:

Experiment 3: The aspartic protease Rhodotorulapepsin and BSA were suspended in 50 mM McIlvaine buffer solution (pH2.5), and then reacted at 4° C. to 60° C. for 1 hour respectively. The experimental conditions are listed in Table 6.

TABLE 6

| Experimental Conditions | BSA Concentration | Rhodotorulapepsin Concentration | pH value | Temper- ature | Buffer Solution |
|---|---|---|---|---|---|
| 1 | 5 mg/ml | 10 µg/ml | 2.5 | 4° C. | 50 mM McIlvaine |
| 2 | 5 mg/ml | 10 µg/ml | 2.5 | 20° C. | 50 mM McIlvaine |
| 3 | 5 mg/ml | 10 µg/ml | 2.5 | 30° C. | 50 mM McIlvaine |
| 4 | 5 mg/ml | 10 µg/ml | 2.5 | 37° C. | 50 mM McIlvaine |
| 5 | 5 mg/ml | 10 µg/ml | 2.5 | 50° C. | 50 mM McIlvaine |
| 6 | 5 mg/ml | 10 µg/ml | 2.5 | 60° C. | 50 mM McIlvaine |

Figure 5C:
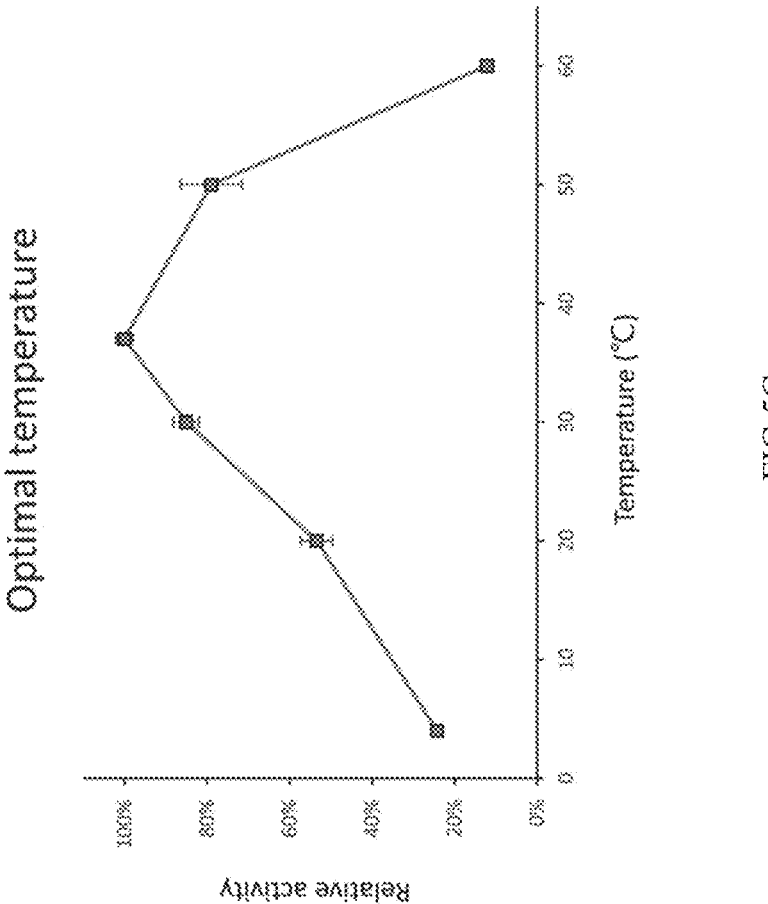
FIG. 5C is an analysis chart showing the relative activity of the aspartic acid protease Rhodotorulapepsin at different temperatures according to Experiment 3.

Referring to FIG. 5C, showing the relative activity analysis chart of the aspartic acid protease Rhodotorulapepsin at different temperatures. As shown in the chart, the aspartic protease Rhodotorulapepsin has good proteolytic activity at a temperature range of 20° C. to 55° C.; preferably, the maximum proteolytic activity of the aspartic protease Rhodotorulapepsin was found at 37° C.; the aspartic protease Rhodotorulapepsin still has relative activity of 93% at 40° C.

(4) Analysis of Thermal Stability:

Experiment 4: The analysis method includes placing buffer solutions respectively including 1 μl of aspartic protease Rhodotorulapepsin at 4° C., 20° C., 30° C., 37° ° C., 50° ° C. and 60° ° C. for 3 hours (see Table 7), and reacting with BSA at 37° C. for 1.5 hours, wherein the concentration of BSA was 5 mg/ml.

TABLE 7

| Experimental Conditions | Rhodotorulapepsin Concentration | pH value | Temperature | Buffer Solution |
|---|---|---|---|---|
| 1 | 10 μg/ml | 2.5 | 4° C. | 50 mM McIlvaine |
| 2 | 10 μg/ml | 2.5 | 20° C. | 50 mM McIlvaine |
| 3 | 10 μg/ml | 2.5 | 30° C. | 50 mM McIlvaine |
| 4 | 10 μg/ml | 2.5 | 37° C. | 50 mM McIlvaine |
| 5 | 10 μg/ml | 2.5 | 50° C. | 50 mM McIlvaine |
| 6 | 10 μg/ml | 2.5 | 60° C. | 50 mM McIlvaine |

Figure 5D:
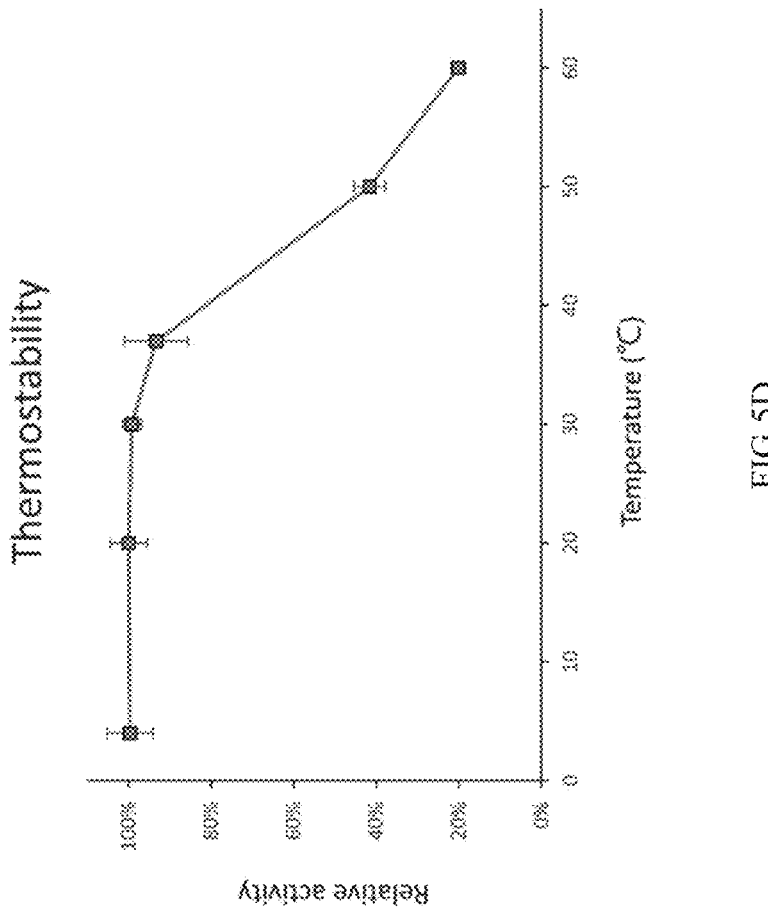
FIG. 5D is an analysis chart showing the stability of the aspartic protease Rhodotorulapepsin at different temperatures according to Experiment 4.

Referring to FIG. 5D, showing a stability analysis chart of the aspartic protease Rhodotorulapepsin at different temperatures. It is shown in the chart that the aspartic protease Rhodotorulapepsin remains stable activity even being placed at 20° C. to 37° C. for 3 hours. The results of the experiments show that the aspartic protease Rhodotorulapepsin according to the present disclosure can hydrolyze protein in the acidic environment of the human stomach, and also has good thermal stability, and therefore is suitable for preparing oral protease supplements stored in room temperature.

Figure 6A:
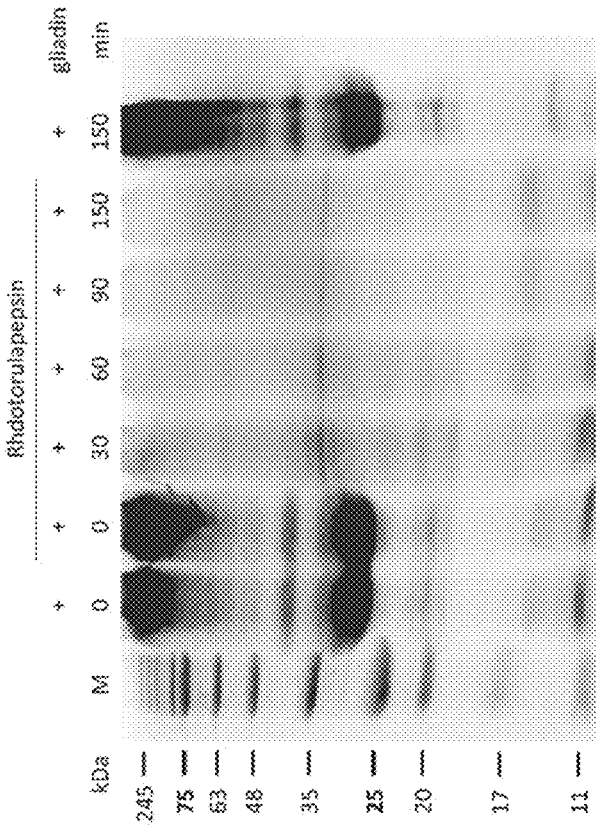
FIG. 6A is the diagram of SDS-PAGE analysis result of residual gliadin after being reacted with the aspartic protease Rhodotorulapepsin for different reaction times according to Experiment 5.
Figure 6B:
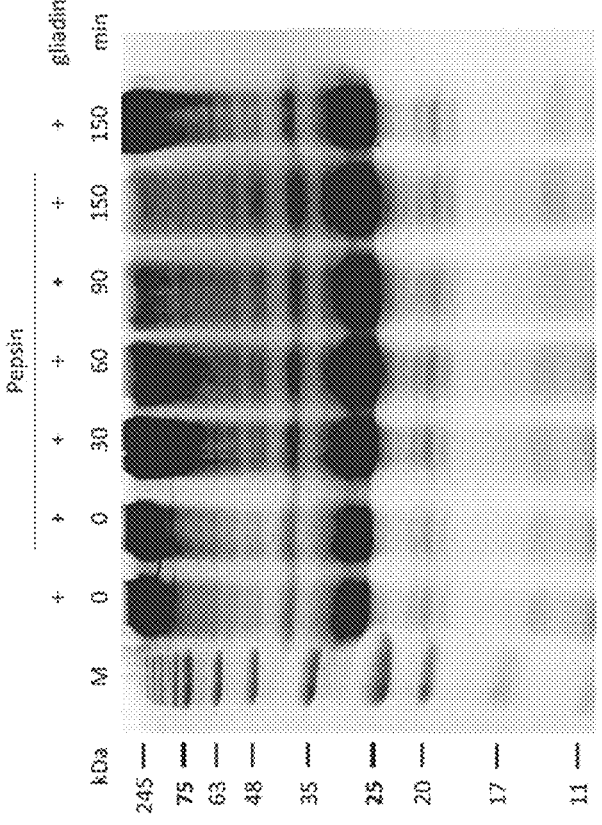
FIG. 6B is the diagram of SDS-PAGE analysis result of residual gliadin after being reacted with pepsin for different reaction times according to Experiment 5.

Analysis of the Ability of the Aspartic Protease Rhodotorulapepsin to Hydrolyze Gliadin Experiment 5: In the present embodiment, to analyze the ability of the aspartic protease Rhodotorulapepsin according to the present disclosure to hydrolyze gliadin, a control group using pepsin as an enzyme was included. In the experiment, the aspartic protease Rhodotorulapepsin and pepsin were used as enzymes, and were respectively mixed with gliadin, wherein the ratio of enzyme to gliadin was 1:500, the pH value of the buffer solution was 3.0, the temperature was 37° C., and the reaction time was 150 minutes, as shown in Table 8. FIG. 6A and FIG. 6B are diagrams showing the results of SDS-PAGE electrophoresis analysis of residual gliadin after being reacted with the aspartic protease Rhodotorulapepsin and pepsin for different reaction times, respectively.

TABLE 8

| Experimental Conditions | Gliadin Concentration | Rhodotorulapepsin Concentration | Pepsin Concentration | pH value | Temperature |
|---|---|---|---|---|---|
| 1 | 10 mg/ml | 20 g/ml | 0 | 3.0 | 37° C. |
| 2 | 10 mg/ml | 0 | 20 μg/ml | 3.0 | 37° C. |

As shown in FIG. 6A, after reaction for 30 minutes, more than 90% of gliadin has been hydrolyzed, that is, the aspartic protease Rhodotorulapepsin can hydrolyze gliadin. Also referring to FIG. 6B, gliadin was not hydrolyzed by pepsin even after 150 minutes of reaction. The experimental results proved that gliadin, i.e., the protein which is included in gluten, can be hydrolyzed by the aspartic acid protease Rhodotorulapepsin according to the present disclosure.

Experiment 6: In the present embodiment, the optimal pH range of the activity of aspartic protease Rhodotorulapepsin on gliadin was further analyzed by monoclonal antibody enzyme-linked immunosorbent assay (R5 Monoclonal Antibody Enzyme-Linked Immunosorbent Assay, R5 ELISA). In this experiment, an R5 ELISA kit purchased from R-Biopharm AG, Germany was utilized. The method includes placing 25 μg/ml of aspartic protease Rhodotorulapepsin and 6.5 mg/ml of gliadin in the buffer solutions of different pH values and shaking the buffer solutions slowly at a temperature of 37° C. for 1 hour. The experimental conditions are listed in Table 9. In this experiment, R5 ELISA was used to analyze the hydrolysis ability of the aspartic protease Rhodotorulapepsin on gliadin at pH 2.5 to pH 7.0. Further, SDS-PAGE electrophoresis analysis was used to analyze the hydrolysis process of the 3-hour reaction at pH 2.5, pH 3.0, and pH 5.0 at a temperature of 37° C.

TABLE 9

| Experimental Conditions | Gliadin Concentration | Rhodotorulapepsin Concentration | pH value | Temperature |
|---|---|---|---|---|
| 1 | 6.5 mg/ml | 25 μg/ml | 2.5 | 37° C. |
| 2 | 6.5 mg/ml | 25 μg/ml | 3.0 | 37° C. |
| 3 | 6.5 mg/ml | 25 μg/ml | 4.0 | 37° C. |
| 4 | 6.5 mg/ml | 25 μg/ml | 5.0 | 37° C. |
| 5 | 6.5 mg/ml | 25 μg/ml | 6.0 | 37° C. |
| 6 | 6.5 mg/ml | 25 μg/ml | 7.0 | 37° C. |

Figure 7A:
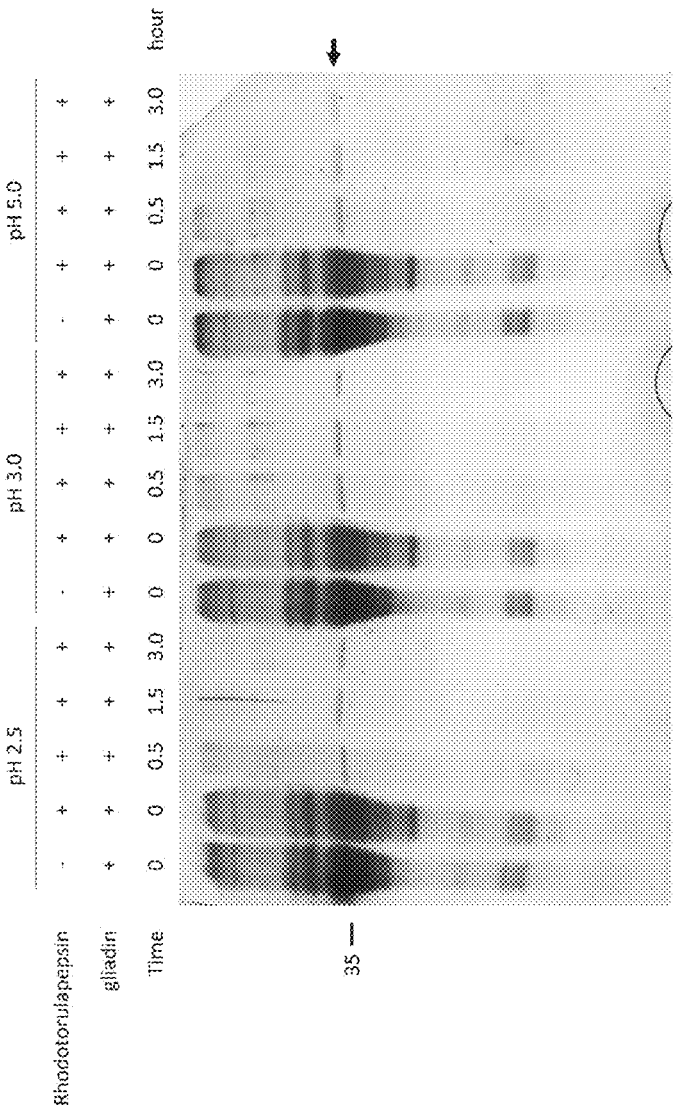
FIG. 7A is the diagram showing the result of SDS-PAGE electrophoresis analysis of gliadin after reacting with the aspartic protease Rhodotorulapepsin under different pH conditions according to Experiment 6.
Figure 7B:
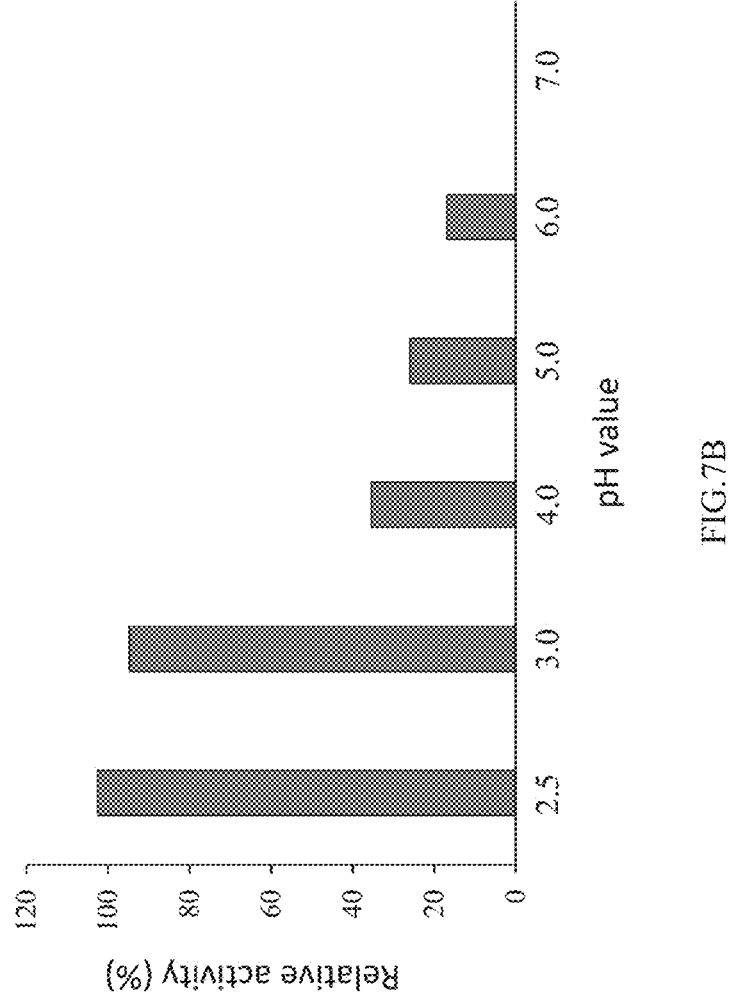
FIG. 7B is the R5 ELISA analysis chart of the gliadin proteolytic ability of the aspartic protease Rhodotorulapepsin under different pH conditions according to Experiment 6.

FIG. 7A is the diagram showing the result of the SDS-PAGE electrophoresis analysis of gliadin after reacting with the aspartic protease Rhodotorulapepsin under different pH conditions. As shown in the figure, gliadin had been hydrolyzed by the aspartic acid protease Rhodotorulapepsin after 0.5 hours of reaction under all of the three pH conditions of pH2.5, pH3.0, and pH5.0. Referring to FIG. 7B, showing the R5 ELISA analysis chart of the ability of the aspartic protease Rhodotorulapepsin according to the present disclosure to hydrolyze gliadin under different pH conditions. It is shown in the chart that the maximum activity of the aspartic protease Rhodotorulapepsin on gliadin was at pH 2.5.

Cleavage Ability of Aspartic Protease Rhodotorulapepsin for Gluten Immune Peptides (26-mer and 33-mer)

In the present embodiment, two gluten immunogenic peptides, including a 26-mer (FLQPQQPFPQQPQQPYPQQPQQPFPQ) from γ-gliadin and a 33-mer (LQLQPFPQPQLPYPQPQLPYPQPQLPYPQPQPF) from α-gliadin, were used to analyze the hydrolysis ability of the aspartic protease Rhodotorulapepsin on gluten immunogenic peptides.

Experiment 7: The method includes the following steps. First, a mixture of 1 mg/ml peptide solution (26-mer) and 25 µg/ml enzyme solution was prepared. The mixture solution was dissolved in buffer solutions of pH3.0 and pH5.0 respectively and reacted for 3 hours at a temperature of 37° C., wherein the experimental conditions are listed in Table 10. Then, the reacted solutions were analyzed by Reverse Phase High-Performance Liquid Chromatography (RP-HPLC).

Experiment 8: The method of this experiment has the same steps as those of Experiment 7, except that the 33-mer peptide solution was used instead of the 26-mer peptide solution, and the experimental conditions are listed in Table 11.

TABLE 10

| Experimental Conditions | 26-mer Concen- tration | Rhodotorulapepsin Concentration | pH value | Buffer Solution |
|---|---|---|---|---|
| 1 | 1 mg/ml | 0 | 3.0 | 50 mM McIlvaine |
| 2 | 1 mg/ml | 25 µg/ml | 3.0 | 50 mM McIlvaine |
| 3 | 1 mg/ml | 25 µg/ml | 5.0 | 50 mM McIlvaine |

TABLE 11

| Experimental Conditions | 33-mer Concen- tration | Rhodotorulapepsin Concentration | pH value | Buffer Solution |
|---|---|---|---|---|
| 1 | 1 mg/ml | 0 | 3.0 | 50 mM McIlvaine |
| 2 | 1 mg/ml | 25 µg/ml | 3.0 | 50 mM McIlvaine |
| 3 | 1 mg/ml | 25 µg/ml | 5.0 | 50 mM McIlvaine |

In addition, according to the present embodiment, a group of control experiments, i.e., Experiment 9 and Experiment 10, were also conducted and pepsin was used as a hydrolytic enzyme to react with gluten immunogenic peptides 26-mer and 33-mer, wherein the experimental conditions are listed in Table 12 and Table 13.

TABLE 12

| Experimental Conditions | 26-mer Concentration | Pepsin Concentration | pH value | Buffer Solution |
|---|---|---|---|---|
| 1 | 1 mg/ml | 0 | 3.0 | 50 mM McIlvaine |
| 2 | 1 mg/ml | 25 µg/ml | 3.0 | 50 mM McIlvaine |
| 3 | 1 mg/ml | 25 µg/ml | 5.0 | 50 mM McIlvaine |

TABLE 13

| Experimental Conditions | 33-mer Concentration | Pepsin Concentration | pH value | Buffer Solution |
|---|---|---|---|---|
| 1 | 1 mg/ml | 0 | 3.0 | 50 mM McIlvaine |
| 2 | 1 mg/ml | 25 µg/ml | 3.0 | 50 mM McIlvaine |
| 3 | 1 mg/ml | 25 µg/ml | 5.0 | 50 mM McIlvaine |

Figure 8A:
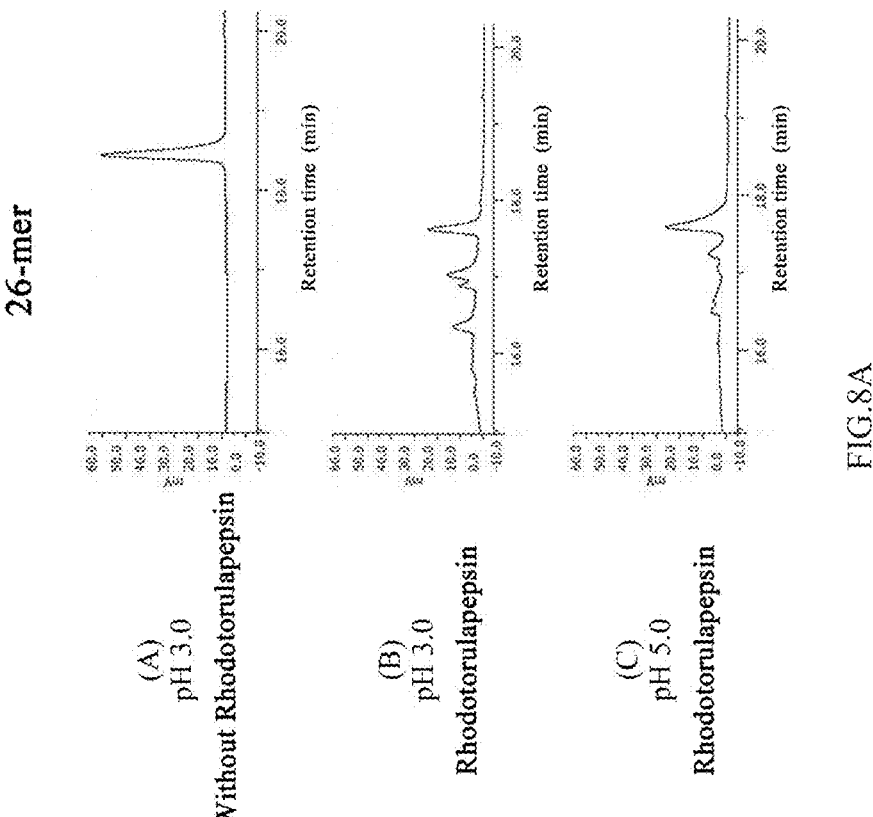
FIG. 8A is the RP-HPLC analysis chart of gluten immunogenic peptide 26-mer after reacting with the aspartic protease Rhodotorulapepsin under various pH conditions according to Experiment 7.
Figure 8B:
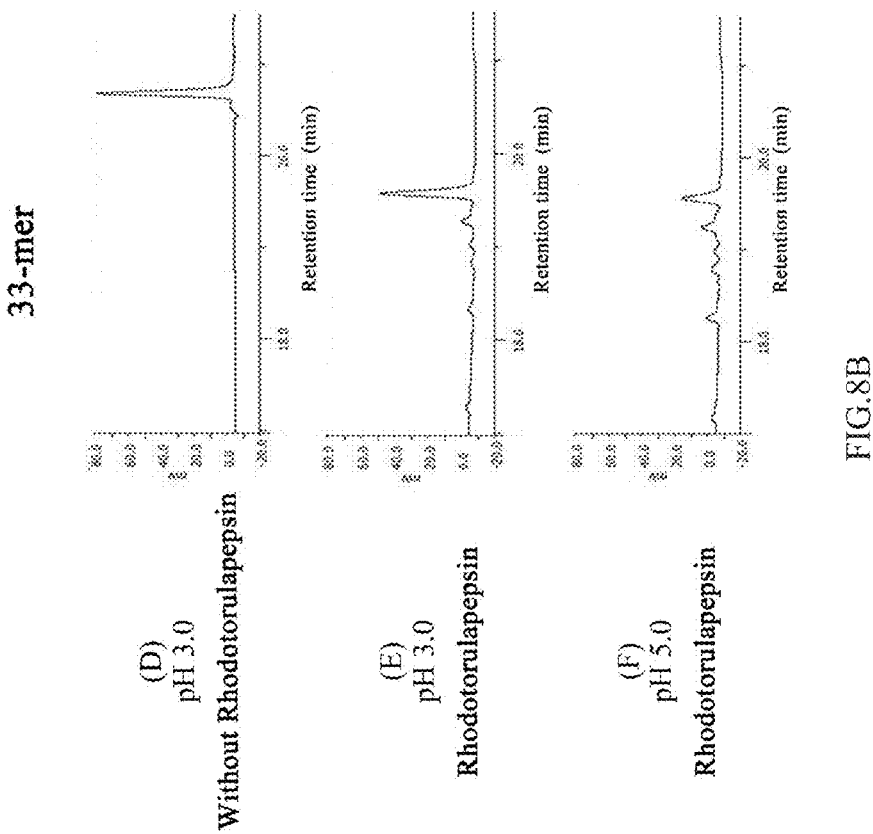
FIG. 8B is the RP-HPLC analysis chart of gluten immunogenic peptide 33-mer after reacting with the aspartic protease Rhodotorulapepsin at pH3.0 and pH5.0 according to Experiment 8.

Referring to FIG. 8A, showing the RP-HPLC analysis chart of gluten immunogenic peptide 26-mer after reacting with the aspartic protease Rhodotorulapepsin under various pH conditions. In FIG. 8A, part (A) is an analysis result for the gluten immunogenic peptide 26-mer solution (pH3.0) without adding the aspartic protease Rhodotorulapepsin, which can represent an initial concentration of gluten immunogenic peptide 26-mer in the solution; part (B) and part (C) are analysis results for the gluten immunogenic peptide 26-mer solutions of pH3.0 and pH5.0 with adding the aspartic protease Rhodotorulapepsin, respectively. The experimental results showed that the optimal pH value for the hydrolysis reaction of the aspartic protease Rhodotorulapepsin on gluten immunogenic 26-mer is at pH 3.0. Referring to FIG. 8B, showing the RP-HPLC analysis chart of gluten immunogenic peptide 33-mer after reacting with the aspartic protease Rhodotorulapepsin under various pH conditions. The experimental results showed that the optimal pH value for the hydrolysis reaction of the aspartic protease Rhodotorulapepsin on gluten immunogenic 33-mer is at pH 5.0.

Figure 9A:
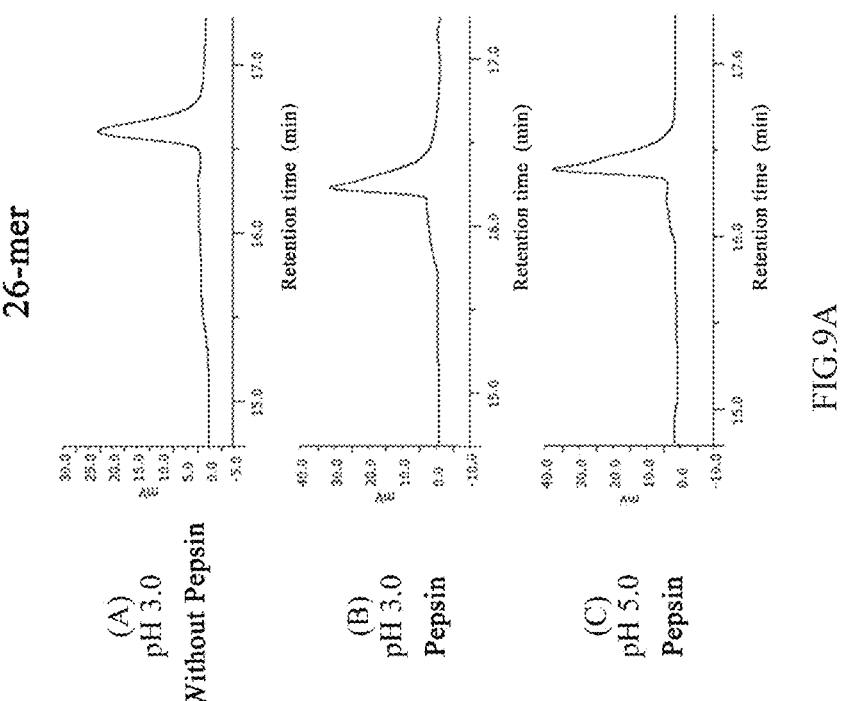
FIG. 9A is the RP-HPLC analysis chart of gluten immunogenic peptide 26-mer after reacting with pepsin at pH3.0 and pH5.0, respectively, according to Experiment 9.
Figure 9B:
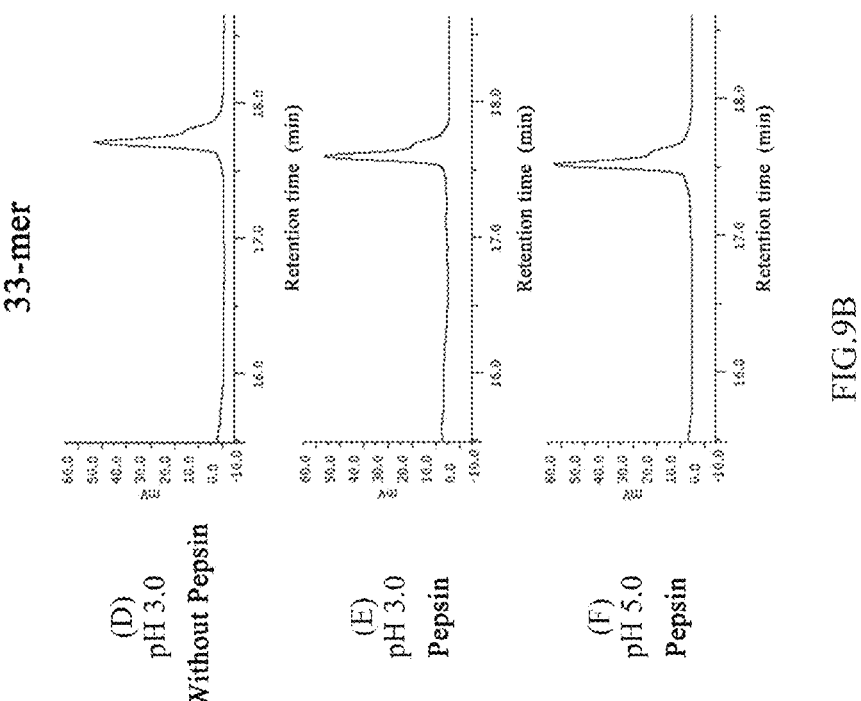
FIG. 9B is the RP-HPLC analysis chart of gluten immunogenic peptide 33-mer after reacting with pepsin at pH3.0 and pH5.0, respective, according to Experiment 10.

Also referring to FIG. 9A and FIG. 9B, wherein, FIG. 9A is the RP-HPLC analysis chart of gluten immunogenic peptide 26-mer after reacting with pepsin at pH3.0 and pH5.0, respectively; FIG. 9B is the RP-HPLC analysis chart of gluten immunogenic peptide 33-mer after reacting with pepsin at pH3.0 and pH5.0, respectively. The experimental results showed that gluten immunogenic peptides 26-mer and 33-mer were not degraded after the same reaction time. That is, pepsin is not capable of hydrolyzing gluten immunogenic peptides 26-mer and 33-mer.

FIG. 10 is a schematic diagram of the epitope on the gluten immunogenic peptide sequence, wherein the T-cell epitopes of gluten immunogenic peptides 26-mer and 33-mer are respectively shown in the figure. In the above experiments, the hydrolysis ability of the aspartic protease Rhodotorulapepsin for gluten immunogenic peptides 26-mer and 33-mer has been proved. In the present embodiment, an analytical instrument was further utilized to identify the small molecule structures of gluten immunogenic peptides 26-mer and 33-mer degraded by aspartic protease Rhodotorulapepsin. Then, the small molecules were compared with the T-cell epitopes to identify the cleavage ability of the aspartic proteases Rhodotorulapepsin on the T-cell epitopes of the gluten immunogenic peptide sequence.

Figure 11A:
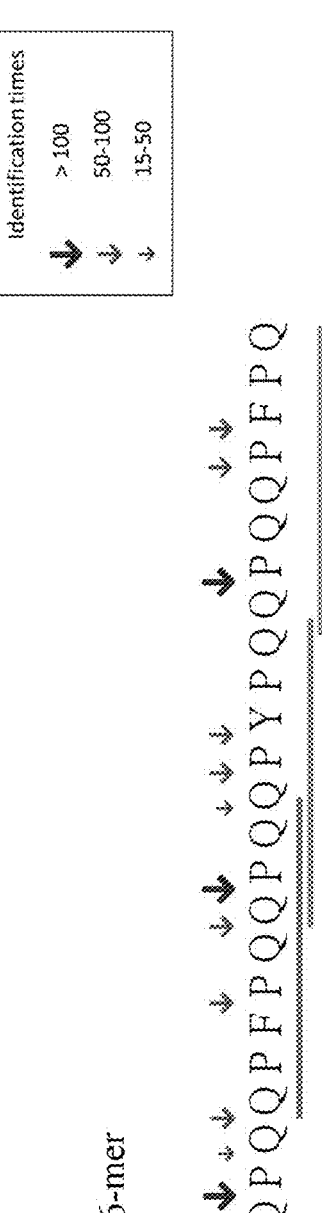
FIG. 11A is a schematic diagram showing the cleavage sites on the gluten immunogenic peptide 26-mer by the aspartic protease Rhodotorulapepsin.
Figure 11B:
FIG. 11B is a schematic diagram showing the cleavage sites on the gluten immunogenic peptide 33-mer by the aspartic protease Rhodotorulapepsin.

In the present embodiment, a liquid chromatography-mass spectrometry/mass spectrometer (LC-MS/MS) was utilized to analyze the cleavage sites on the two gluten immunogenic peptides 26-mer and 33-mer by the aspartic protease Rhodotorulapepsin. The method includes the following steps. First, it is to collect the aforementioned reaction solutions including gluten immunogenic peptides 26-mer and 33-mer degraded by the aspartic protease Rhodotorulapepsin at pH3.0. Then, the cleavage sites are analyzed by using LC-MS/MS. Referring to FIGS. 11A and 11B, respectively showing the cleaved sites on the gluten immunogenic peptides 26-mer and 33-mer by the aspartic protease Rhodotorulapepsin as determined by LC-MS/MS Analysis. In the figures, the underlined peptide sequences represent the T-cell epitopes, and the arrows represent the cleavage sites where the peptide sequence is cleaved, wherein the arrows of different thicknesses represent the number of identification times. In this example, the gluten immunogenic peptide 26-mer was identified 827 times; the gluten immunogenic peptide 33-mer was identified 1070 times. After statistical analysis, the predominant site of the gluten immunogenic peptide 26-mer cleaved by the aspartic protease Rhodotorulapepsin is PQQ↓PXP(X=F/Y), and the predominant site of the gluten immunogenic peptide 33-mer cleaved by the aspartic protease Rhodotorulapepsin is PQL↓PYP. As shown in the figure, the T-cell epitopes of the gluten immunogenic peptides 26-mer and 33-mer can be effectively removed by utilizing the two cleavage sites. Therefore, according to the experimental results, it has been proved that the aspartic protease Rhodotorulapepsin can effectively cleave the T-cell epitopes on the gluten immunogenic peptides 26-mer and 33-mer, thereby avoiding adverse reactions caused in the human body by the gluten immunogenic peptides 26-mer and 33-mer, and can be used as an oral protease to hydrolyze gluten.

Figure 12:
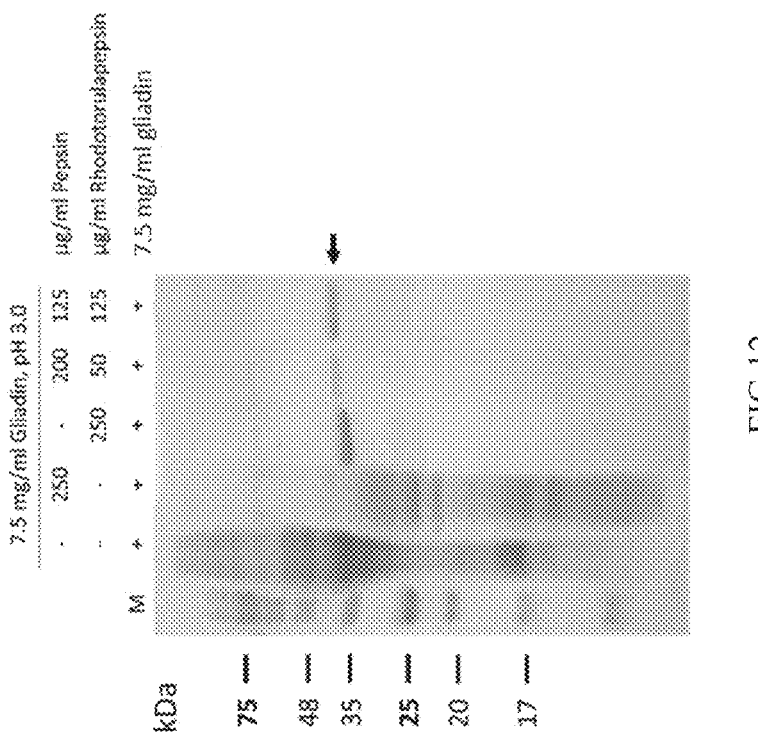
FIG. 12 is the diagram showing the result of the SDS-PAGE electrophoresis analysis of gliadin after reacting with the mixture of the aspartic protease Rhodotorulapepsin and pepsin according to Experiment 11.

The Hydrolysis Ability of the Aspartic Protease Rhodotorulapepsin for Gluten in an Environment that Simulates the Human Stomach Experiment 11: In the present embodiment, the aspartic protease Rhodotorulapepsin was further mixed with pepsin and then placed in an environment that simulates the human stomach to test the hydrolysis ability thereof to hydrolyze gliadin. The method includes the following steps. First, the aspartic protease Rhodotorulapepsin and pepsin were mixed in four ratios of 250:0, 50:200, 125:125, and 0:250 (as shown in Table 14), and the total concentration of the aspartic protease Rhodotorulapepsin and pepsin was 250 μg/ml. Next, 7.5 mg/ml of gliadin was added to the mixture of the aspartic protease Rhodotorulapepsin and pepsin and reacted at pH 3.0 for 3 hours. Then, the degrading process of gliadin was analyzed with SDS-PAGE. FIG. 12 is the diagram showing the result of the SDS-PAGE electrophoresis analysis of gliadin after reacting with the mixture of the aspartic protease Rhodotorulapepsin and pepsin. The electrophoresis analysis results of FIG. 12 are corresponding to the five experimental conditions shown in Table 14.

TABLE 14

| Experimental Conditions | Gliadin Concentration | Pepsin Concentration | Rhodotorulapepsin Concentration | Electrophoretic Analysis Result |
|---|---|---|---|---|
| 1 | 7.5 mg/ml | 0 | 0 | Lane 1 |
| 2 | 7.5 mg/ml | 250 μg/ml | 0 | Lane 2 |
| 3 | 7.5 mg/ml | 0 | 250 μg/ml | Lane 3 |
| 4 | 7.5 mg/ml | 200 μg/ml | 50 μg/ml | Lane 4 |
| 5 | 7.5 mg/ml | 125 μg/ml | 125 μg/ml | Lane 5 |

As shown in Lane 2 of FIG. 12, when only 250 μg/ml of pepsin was included in the enzyme mixture, gliadin was not completely hydrolyzed; in contrast, as shown in Lane 3 of FIG. 12, even only 250 μg/ml of aspartic protease Rhodotorulapepsin was included in the enzyme mixture, gliadin was completely hydrolyzed. In addition, as shown in Lane 4 of FIG. 12, when 200 μg/ml of pepsin and 50 μg/ml of aspartic protease Rhodotorulapepsin were reacted together with gliadin, gliadin can also be completely hydrolyzed. Therefore, according to the experimental results, the aspartic protease Rhodotorulapepsin can effectively hydrolyze gliadin in the presence of pepsin in an environment that simulates the human stomach.

Experiment 12: In the present embodiment, this experiment was performed to analyze the ability of the aspartic protease Rhodotorulapepsin to hydrolyze gliadin in an environment of pH2.5 that simulates the human stomach. The experimental conditions are listed in Table 15, wherein since the maximum concentration of pepsin in the human body was about 1 mg/ml, therefore, the concentration of pepsin used in this experiment was set at 1 mg/ml. The buffer solution used in this experiment included 10 mM HCl, 15 mM KCl, and 50 mM NaCl and had a pH value of pH2.5. Depending on the conditions listed in Table 15, different concentrations of pepsin and the aspartic protease Rhodotorulapepsin were added into the buffer solutions and reacted for 1.5 hours.

TABLE 15

| Experimental Conditions | Gliadin Concentration | Pepsin Concentration | Rhodotorulapepsin Concentration | pH value |
|---|---|---|---|---|
| 1 | 25 mg/ml | 0 | 0 | 2.5 |
| 2 | 25 mg/ml | 1 mg/ml | 0 | 2.5 |

TABLE 15-continued

| Experimental Conditions | Gliadin Concentration | Pepsin Concentration | Rhodotorulapepsin Concentration | pH value |
|---|---|---|---|---|
| 3 | 25 mg/ml | 0 | 0.05 mg/ml | 2.5 |
| 4 | 25 mg/ml | 1 mg/ml | 0.05 mg/ml | 2.5 |

Figure 13A:
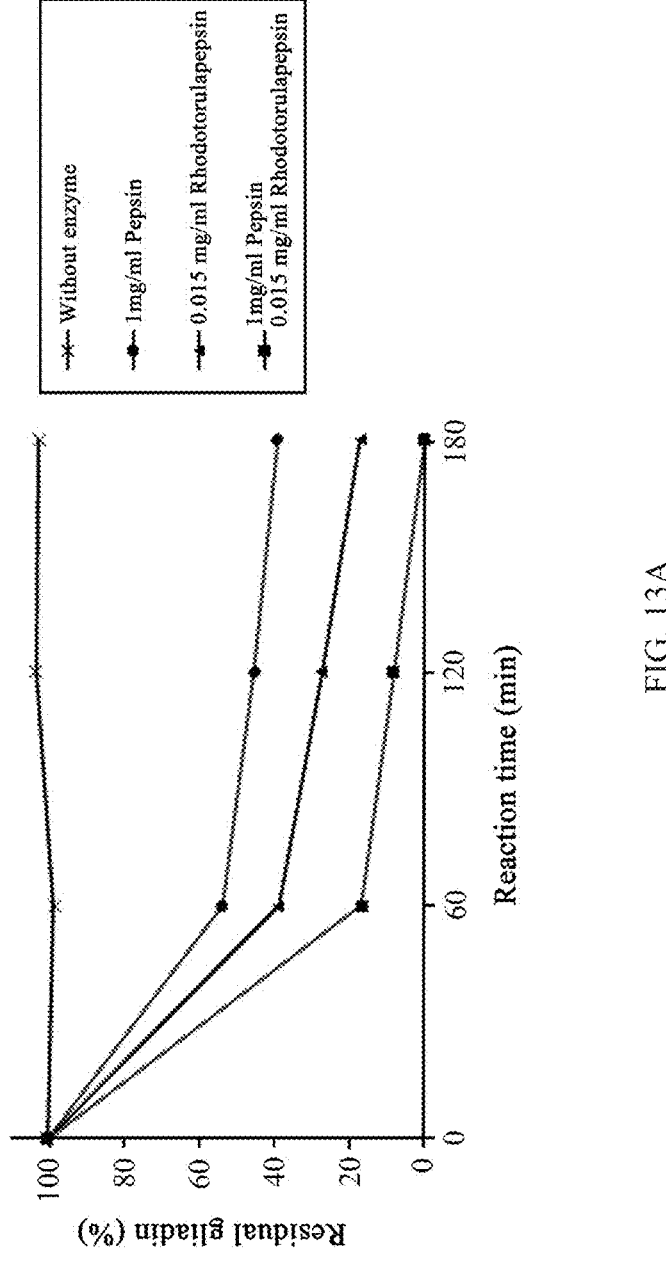
FIG. 13A is the ELISA analysis chart of the residual amount of gliadin in each solution of Experiment 12 at different times.
Figure 13B:
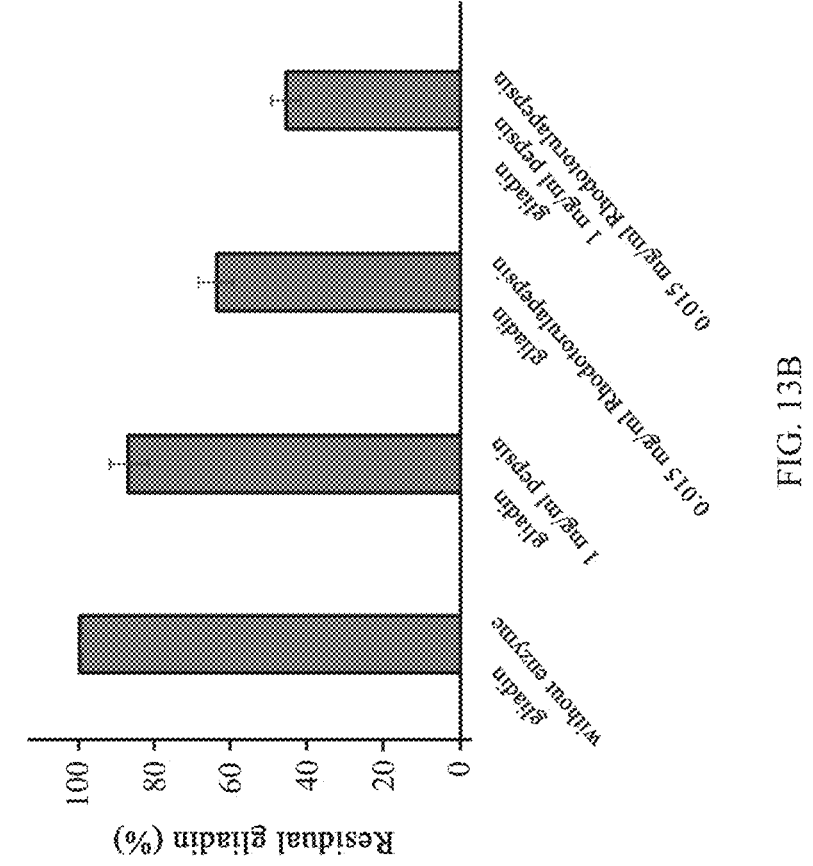
FIG. 13B is a chart showing the residual amount of gliadin with a reaction time of 1.5 hours according to Experiment 12.

Referring to FIG. 13A and FIG. 13B, wherein FIG. 13A is the ELISA analysis chart of the residual amount of gliadin in each solution of the experimental conditions at different times; FIG. 13B is a chart showing the residual amount of gliadin with a reaction time of 1.5 hours. As shown in FIG. 13B, the relative activity of the simulated gastric acid environment to hydrolyze gliadin is 13%, while the relative activity thereof is increased by 54% after adding the aspartic protease Rhodotorulapepsin. From the experimental results, the aspartic protease Rhodotorulapepsin is resistant to pepsin hydrolysis, in other words, the aspartic acid protease Rhodotorulapepsin will not be hydrolyzed by pepsin in the human stomach and can assist pepsin in the simulating gastric acid environment to hydrolyze gliadin.

The present disclosure provides another embodiment, which includes a drug for treating chronic autoimmune diseases caused by gluten, wherein the drug includes the aspartic protease of the present disclosure and is used for treating conditions such as celiac disease, gluten sensitivity, or gluten intolerance. In addition, the embodiment provides a method for treating gluten intolerance. The method includes administering the drug including the aspartic protease of the present disclosure to a patient in need.

The present disclosure further provides another embodiment, which includes an enzyme supplement (or enzyme supplement food), wherein, the enzyme supplement includes the aspartic protease according to the present disclosure, and is used for metabolizing gluten-containing food, to relieve celiac disease, gluten sensitivity, or gluten intolerance.

The aspartic protease according to the present disclosure is also suitable for use in food processing to remove or reduce gluten content in food or drink.

As explained above, the aspartic protease according to the present disclosure has good thermal stability at a temperature range of 20° C. to 37° C. Therefore, the enzyme supplement or medicine prepared by using the aspartic protease according to the present disclosure can be stored at room temperature without refrigeration, improving the convenience of use for patients with celiac disease and other diseases.

The present invention has been described in terms of particular embodiments found or proposed by the inventor to comprise preferred methods for the practice of the invention. It will be appreciated by those skilled in the art that, in light of the present disclosure, numerous modifications and changes can be made in the particular embodiments exemplified without departing from the intended scope of the invention. Moreover, due to biological functional equivalency considerations, changes can be made in methods, structures, and compounds without affecting the biological action in kind or amount. All such modifications are intended to be included within the scope of the appended claims.

What is claimed is:

1. A method for treating gluten intolerance by utilizing an aspartic protease comprising an amino acid sequence having at least 70% identity to the sequence identified as SEQ ID NO: 1, wherein the aspartic protease has gluten-degrading activity between pH 2.0 and pH 4.0, comprising administering the aspartic protease to a patient in need.

2. The method according to claim 1, wherein the amino acid sequence of the aspartic protease has at least 80% identity to the sequence identified as SEQ ID NO: 1.

3. The method according to claim 1, wherein the amino acid sequence of the aspartic protease has at least 90% identity to the sequence identified as SEQ ID NO: 1.

4. The method according to claim 1, wherein the optimum pH value of utilizing the aspartic protease on degrading gliadin is pH 2.5.

5. The method according to claim 1, further comprising utilizing the aspartic protease to cleave epitopes on gluten immunogenic peptides 26-mer or 33-mer.

6. The method according to claim 1, wherein the aspartic protease further comprises a histidine tag.

* * * * *